(12) United States Patent
Li et al.

(10) Patent No.: US 7,304,057 B2
(45) Date of Patent: Dec. 4, 2007

(54) SUBSTITUTED 6-MEMBERED N-HETEROCYCLIC COMPOUNDS AND METHOD FOR THEIR USE AS NEUROLOGICAL REGULATOR

(75) Inventors: Song Li, Beijing (CN); Aihua Nie, Beijing (CN); Beifen Shen, Beijing (CN); Lili Wang, Beijing (CN); Wuhong Pei, Beijing (CN); Junhai Xiao, Beijing (CN); Songcheng Yang, Beijing (CN); Liuhong Yun, Beijing (CN); Hongying Liu, Beijing (CN); Cuiling Shu, Beijing (CN); Hongxia Wang, Beijing (CN); Zihe Rao, Beijing (CN)

(73) Assignee: Institute of Pharmacology and Toxicology Accademy of Military Medical Sciences P.L.A. China, Beijing (CN)

( * ) Notice: Subject to any disclaimer, the term of this patent is extended or adjusted under 35 U.S.C. 154(b) by 270 days.

(21) Appl. No.: 10/497,876

(22) PCT Filed: Dec. 5, 2002

(86) PCT No.: PCT/CN02/00871

§ 371 (c)(1),
(2), (4) Date: Feb. 10, 2005

(87) PCT Pub. No.: WO03/048142

PCT Pub. Date: Jun. 12, 2003

(65) Prior Publication Data

US 2005/0130958 A1  Jun. 16, 2005

(30) Foreign Application Priority Data

Dec. 6, 2001  (CN) .............................. 01 1 42744

(51) Int. Cl.
*C07D 417/12* (2006.01)
*C07D 279/12* (2006.01)
*A61K 31/541* (2006.01)
*A61K 31/54* (2006.01)

(52) U.S. Cl. .............................. 514/227.5; 514/227.8; 544/58.2

(58) Field of Classification Search ............... 544/58.2; 514/227.8, 227.5
See application file for complete search history.

(56) References Cited

U.S. PATENT DOCUMENTS 5,798,355 A  8/1998 Steiner et al.

FOREIGN PATENT DOCUMENTS

| WO | WO96/40140 | 12/1996 |
| WO | WO9914988 | 4/1999 |
| WO | WO9962880 | 12/1999 |
| WO | WO00/09104 | 2/2000 |
| WO | WO00/09109 | 2/2000 |

OTHER PUBLICATIONS

Starzl, T.E., et al. "FK-506: A potential breakthrough in immunosuppression". *Transplant Proc*, 1987, 19: S3-S104.
Maki N., et al. "Complementary DNA encoding the human T-cell FK506-binding protein, a peptidylprolyl cis-trans isomerase distinct from cyclophilin". *Proc Natl Acad Sci USA*, 1990, 87:5440-5443.
Steiner, J.P, et al. "High brain densities of the immunophilin FKBP colocalized with calcineurin" *Nature*, 1992, 358: 584-587.
Sharkey, J., et al. "Immunophilins mediate the neuroprotective effects of FK506 in focal celebral ischaemia." *Nature*, 1994, 371: 336-339.
Lyons, W.E., et al. "Immunosuppresant FK506 promotes neurite outgrowth in cultures of PC-12cells and sensory ganglia". *ProcNatl Acad Sci USA*, 1994, 91: 3191-3195.
Gold, B.G., et al. "The immunosuppressant FK506 increases functional recovery and nerve regeneration following peripheral nerve injury". *Restor Neurol Neurosci*, 1994, 6: 287-296.
Gold B.G., et al. "The immunosuppressant FK506 increases the rate of axonal regeneration in rat sciatic nerve." *J Neurosci*, 1995, 15: 7509-7516.
Kopp J B, et al. "Cellular and molecular mechanisms of cyclosporin nephrotoxicity." *J Am Soc Nephrol*, 1990, 1:162-179.
De Groen, P.C., et al. "Central nervous system toxicity after liver transplantation." *N Engl J Med*, 1987, 317: 861-866.
Kahan, B.D. "Drug therapy: cyclosporine". *N Engl J Med*, 1989, 321: 1725-1738.

*Primary Examiner*—Kahsay Habte
(74) *Attorney, Agent, or Firm*—Ladas & Parry LLP (57) ABSTRACT

This invention relates to substituted 6-membered N-Herterocyclic neurotrophic compounds of formula (I) or pharmaceutically acceptable salts or hydrates thereof, wherein $R_1$, $R_2$, X, Y, and Z are as defined in the description; their preparation methods, compositions comprising the same, and their use as inhibitors of FK560 binding proteases activity for treating and preventing neurodegenerative diseases and other nerve disorders associated with nerve injuries or other related diseases

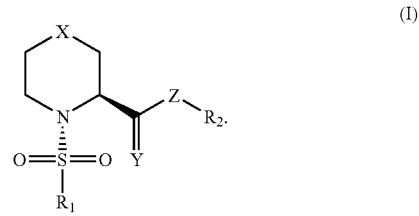

(I)

3 Claims, 3 Drawing Sheets

SUBSTITUTED 6-MEMBERED N-HETEROCYCLIC COMPOUNDS AND METHOD FOR THEIR USE AS NEUROLOGICAL REGULATOR

This application is a PCT application, PCT/CN02/00871, which was filed on Dec. 5, 2002, and claims the priority date of Dec. 6, 2001 in P.R. China.

FIELD OF THE INVENTION

This invention relates to substituted 6-membered N-Herterocyclic compounds, their preparation methods, compositions comprising the same, and their use as inhibitors of FK560 binding proteins (FKBPs) enzyme activity for treating and preventing neurodegenerative diseases and other nerve disorders associated with nerve injury or other related diseases.

BACKGROUND OF THE RELATED ART

Neurodegenerative disease is a kind of progressive disease associated with age including, for example, Alzheimer's disease, Parkinson's disease, Huntington's disease and amyotrophic lateral sclerosis (ALS). At present there are no effective methods for treating this kind of disease due to its unclear mechanism and complicated invasion cause.

As very important biological active molecules existed in the nerve system, neurotrophic factors (NTFs), such as nerve growth factor (NGF), can effectively promote regeneration and functional recovery of injured neuraxon. So, neurotrophic factors are considered as a potential drug for treating neurodegenerative diseases. However, effective clinical application of such neurotrophic molecules is restricted due to the insurmountable low bioavailability and specificity of large protein molecules.

In addition to the immunity system, FKBPs have been found to be present at high concentrations in the central nervous system. It has been found that the immunosuppressant FK506, as a potent inhibitor of FKBPs, can remarkably promote the neurite outgrowth and the nerve fiber differentiation, and show excellent blood-brain barrier penetrability and bioavailability[4]. However, when administered chronically, the immunosuppressant FK506 induces a number of potential side and toxic actions, including nephrotoxicity, such as impairment of glomerular filtration and irreversible interstitial fibrosis; and neurological deficits, such as involuntary tremors and non-specific cerebral angina.

OBJECT OF THE INVENTION

The object of the present invention is to provide non-immunosuppressive small molecule compounds acting on FKBPs for promoting the nerve outgrowth and regeneration in various neuropathological situations including neurological diseases associated with neurodegeneration, such as Alzheimer's disease, Parkinson's disease and amyotrophic lateral sclerosis, and neurological disorders caused by various physical injuries (such as mechanical injuries or concussions) or other diseases (such as diabetes or autoimmune acquired diseases).

BRIEF DESCRIPTION OF THE INVENTION

It has been found that the compound of formula (I) may be used as FKBPs for promoting the nerve outgrowth and regeneration in various neuropathological situations. Thus, the compound of formula (I) could be used to prevent and/or treat neurological diseases associated with neurodegeneration.

In the first aspect, the present invention relates to a compound of formula (I):

or a pharmaceutically acceptable salt or a hydrate thereof, wherein:

X is $CH_2$, O, S, SO, $SO_2$ or $NR_3$, wherein $R_3$ is hydrogen or $C_1$-$C_3$ alkyl;

Y is O or S;

Z is $CH_2$, O or $NR_4$, wherein $R_4$ is hydrogen or $C_1$-$C_6$ alkyl;

$R_1$ is straight or branched chain $C_1$-$C_8$ alkyl, straight or branched chain $C_2$-$C_8$ alkenyl, $C_3$-$C_8$ cycloalkyl, $C_5$-$C_7$ cycloalkenyl, or $Ar_1$, wherein alkyl or alkenyl chain may be unsubstituted or substituted with one or more of the following groups: $C_3$-$C_8$ cycloalkyl, $C_5$-$C_7$ cycloalkenyl, or $Ar_2$;

$R_2$ is straight or branched chain $C_1$-$C_{10}$ alkyl, straight or branched chain $C_2$-$C_{10}$ alkenyl, $C_3$-$C_8$ cycloalkyl, $C_5$-$C_7$ cycloalkenyl, and $Ar_1$, wherein alkyl or alkenyl chain may be unsubstituted or substituted with one or more of the following groups: $C_3$-$C_8$ cycloalkyl, $C_5$-$C_7$ cycloalkenyl, or $Ar_2$, in addition, wherein a part of carbon atoms of alkyl or alkenyl can be replaced by nitrogen or oxygen atoms;

$Ar_1$ and $Ar_2$ are independently selected from mono-, di-, or tricyclic aromatic carbocyclic ring and heterocyclic ring containing 1 to 6 heteroatoms selected from a group consisting of O, S and N, wherein each single ring is 5-membered or 6-membered, and said ring may be unsubstituted or substituted in one to five position(s) with 1 to 3 following groups: halogens, nitro, hydroxy, hydroxymethyl, trifluoromethyl, trifluoromethoxyl, straight or branched chain $C_1$-$C_6$ alkyl, straight or branched chain $C_2$-$C_6$ alkenyl, $C_1$-$C_4$ alkoxy, $C_2$-$C_4$ alkenoxy, phenoxy, benzyloxy, carboxyl or amino, wherein the relative configuration of group —$SO_2Ar_1$ to group —$COZR_2$ is a trans-configuration.

In another aspect, the present invention relates to a pharmaceutical composition comprising at least one compound of formula (I) or a pharmaceutically acceptable salt or a solvate thereof, and pharmaceutically acceptable carriers or excipients.

In a further aspect, the present invention relates to the a method of preparing a compound of formula (I) or a pharmaceutically acceptable salt or a solvate thereof, comprising:

(i) reacting compound 1 with epoxy ethane to obtain compound 2,

(ii) dissolving compound 2 in hydrochloric acid to obtain compound 3,

(iii) dissolving compound 3 in methanol and passing thereinto dry HCl gas to obtain compound 4, (iv) reacting compound 4 with bases in polar non-protonic solvents, and then undergoing cyclization in the solution of HCl in ethyl ethyl or ethanol to obtain compound 5, (v) reacting compound 5 with $R_1COCl$ to obtain compound 6, (vi) reacting compound 6 with alkali metal hydroxides to obtain compound 7, (vii) reacting compound 7 with $R_2OH$ or amino acid ester hydrochlorid, DCC, DMAP or TEA to obtain the compound 8, and (viii) oxidizing compound 7 with MCPBA to obtain the compound of formula (I).

If desired, the obtained compound of formula (I) can be converted to a pharmaceutically acceptable salt using a suitable acid or base.

In a still further aspect, the present invention relates to the use of at least one compound of formula (I) or a pharmaceutically acceptable salt or a hydrate thereof in preparing a drug for treating and/or preventing diseases associated with nerve pathological changes.

The present invention also relates to a method for preventing and/or treating diseases associated with nerve pathological changes comprising administering a therapeutically effective amount of a compound of formula (I) or a pharmaceutically acceptable salt or a hydrate thereof to the patients in need.

DETAILED DESCRIPTION OF THE INVENTION

According to the invention, a preferred embodiment is the compound of formula (I), or a pharmaceutically acceptable salt or a hydrate thereof:

X is S, SO, or $SO_2$;
Y is O;
Z is O or NH,
$R_1$ is aromatic group $Ar_1$;
$R_2$ is selected from the group consisting of straight or branched chain $C_1$-$C_{10}$ alkyl, straight or branched chain $C_2$-$C_{10}$ alkenyl, $C_3$-$C_8$ cycloalkyl, $C_5$-$C_7$ cycloalkenyl, and $Ar_1$, wherein alkyl or alkenyl chain may be unsubstituted or substituted with one or more of the following groups: $C_3$-$C_8$ cycloalkyl, $C_5$-$C_7$ cycloalkenyl, or $Ar_2$, in addition, wherein a part of carbon atoms of alkyl or alkenyl can be replaced by nitrogen or oxygen atoms;
$Ar_1$ and $Ar_2$ are independently selected from a cyclic or fused cyclic ring and includes a mono-, bi-or tricyclic, carbo-or hetercyclic ring, wherein a ring is consisted by 5-6 elements, the heteroatom consisting of heterocyclic is selected from nitrogen, sulfur or oxygen; wherein the ring is either unsubstituted or substituted in one to five position(s) with halo, nitro, hydroxyl, hydoxylmethyl, trifluoromethyl, trifluoromethoxyl, $C_1$-$C_6$ straight or branched chain alkyl, $C_2$-$C_6$ straight or branched chain alkenyl, $C_1$-$C_4$ alyoxy, $C_2$-$C_4$ alkenyloxy, phenoxy, benzyloxy, carboxyl and amino, wherein the relative configuration of group —$SO_2Ar_1$ to group —$COZR_2$ is a trans-configuration.

Preferred compounds or their pharmaceutically acceptable salts or hydrates of the invention include:

2-{[(3R)-4-(4-toluenesulfonyl)thiomorpholine-3-carbonyl]amino}-3-phenyl-propionic acid benzyl ester,
2-{[(3R)-4-(4-toluenesulfonyl)thiomorpholine-3-carbonyl]amino}-3-methyl-butyric acid benzyl ester,
2-{[(3R)-4-(4-toluenesulfonyl)thiomorpholine-3-carbonyl]amino}-4-methyl-pentanoic acid benzyl ester,
2-{[(3R)-4-(4-toluenesulfonyl)thiomorpholine-3-carbonyl]amino}-4-methyl-pentanoic acid ethyl ester,
(3R)-4-(4-toluenesulfonyl)thiomorpholine-3-carboxylic acid [3-(pyridin-3-yl)]-propyl ester,
(3R)-4-(4-toluenesulfonyl)thiomorpholine-3-carboxylic acid [N-methyl-N-(pyridin-2-yl)]-ethyl ester,
(3R)-4-(4-toluenesulfonyl)thiomorpholine-3-carboxylic acid phenylpropyl ester,
(3R)-4-(4-toluenesulfonyl)thiomorpholine-3-carboxylic acid (2-trifluoromethyl)-phenylethyl ester,
(3R)-4-(4-toluenesulfonyl)thiomorpholine-3-carboxylic acid (N-methyl-N-benzyl)-ethyl ester,
(3R)-4-(4-toluenesulfonyl)thiomorpholine-3-carboxylic acid (3-phenyl)-allyl ester,
(3R)-4-(4-toluenesulfonyl)thiomorpholine-3-carboxylic acid (3-cyclohexyl)-propyl ester,
(3R)-4-(4-toluenesulfonyl)thiomorpholine-3-carboxylic acid (1,3-diphenyl)-propyl ester,
(3R)-4-(4-toluenesulfonyl)thiomorpholine-3-carboxylic acid (1-p-methoxyphenyl-3-phenyl)-propyl ester,
(3R)-4-(4-toluenesulfonyl)thiomorpholine-3-carboxylic acid (1-p-fluorophenyl-3-phenyl)-propyl ester,
(3R)-4-(4-toluenesulfonyl)thiomorpholine-3-carboxylic acid [3-phenyl-1-(thiophen-2-yl)]-propyl ester,
(3R)-4-(4-toluenesulfonyl)thiomorpholine-3-carboxylic acid [3-(6-methyl-pyridin-2-yl)]-propyl ester,
(3R)-4-(4-toluenesulfonyl)thiomorpholine-3-carboxylic acid [N-ethyl-N-3-(3-methyl)phenyl]-ethyl ester,
(3R)-4-(4-toluenesulfonyl)thiomorpholine-3-carboxylic acid (1,3-diphenylmethyloxy)-isopropyl ester,
(3R)-4-(4-toluenesulfonyl)thiomorpholine-3-carboxylic acid (thiophen-2-yl)-ethyl ester,
(3R)-4-(4-toluenesulfonyl)thiomorpholine-3-carboxylic acid (3-phenoxy)-propyl ester,
(3R)-4-(4-toluenesulfonyl)thiomorpholine-3-carboxylic acid [1-phenyl-1-(3-tolyl)]-methyl ester,
(3R)-4-(4-toluenesulfonyl)thiomorpholine-3-carboxylic acid [1-methyl-1-(3-trifluoromethylphenyl)]-methyl ester,
(3R)-4-(4-toluenesulfonyl)thiomorpholine-3-carboxylic acid 4-nitrobenzyl ester,
(3R)-4-(4-toluenesulfonyl)thiomorpholine-3-carboxylic acid 2-methoxybenzyl ester,
(3R)-4-(4-toluenesulfonyl)thiomorpholine-3-carboxylic acid (3-ethoxy-2-methoxy)-benzyl ester,
(3R)-4-(4-toluenesulfonyl)thiomorpholine-3-carboxylic acid 4-phenylbenzyl ester, and
2-{[(3R)-1,1-dioxo-4-(4-toluenesulfonyl)thiomorpholine-3-carbonyl]amino}-4-methyl-pentanoic acid ethyl ester.

The compounds of the present invention can be used in the form of salts derived from inorganic or organic acids or inorganic or organic bases. Such acid salts include, but are not limited to, the following salts: hydrochloride, hydrobromide, hydriodide, nitrate, sulfate, bisulfate, phosphate, hydrophosphate, acetate, propionate, butanoate, oxalate, trimethyl acetate, adipate, alginate, lactate, citrate, tartrate, succinate, maleate, fumarate, picrate, aspartate, gluconate, benzoate, methanesulfonate, ethanesulfonate, benzenesulfonate, tosylate and dihydroxynaphthoate. Such base salts include, but are not limited to, the following salts: ammonium salts, alkali metal salts such as sodium and potassium salts, alkaline earth metal salts such as calcium and magnesium salts, salts derived from organic bases such as dicyclohexylamine and N-methyl-D-glucamine salts, and salts derived from amino acids such as arginine and lysine salts.

According to the present invention, the pharmaceutical composition includes an effective amount of a compound of formula (I) or a pharmaceutical salt or a hydrate thereof, and one or more suitable pharmaceutically acceptable carriers. The pharmaceutically acceptable carrier is selected from, but is not limited to, the following carriers: ion exchanger, aluminum oxide, aluminum stearate, lecithin, serum protein (e.g. human serum protein), buffer substance (e.g. phosphate), glycerol, sorbic acid, potassium sorbate, mixture of partial glycerides of saturated vegetable fatty acids, water, salt or electrolyte (e.g. protamine sulfate, disodium hydrogen phosphate, potassium hydrogen phosphate, sodium chloride, zinc salt), colloidal silicon oxide, magnesium trisilicate, polyvinylpyrrolidone, cellulose, polyethylene glycol, sodium carboxymethycellulose, polyacrylate, beeswax, polyethylene-polyoxopropylene block polymer and lanolin.

The compound of the present invention is a kind of potent neuroregulation molecules having an affinity for FKBPs. In contrast to FK506, the compound of the present invention does not result in immunosuppression. The neuroregulation activity comprises, but is not limited to, repair of damaged neurons, promotion of neuronal regeneration, prevention of neurodegeneration and treatment of neurological disorders associated with neurodegeneration or peripheral nerve pathological changes. The neurological disorders that may be treated include, but are not limited to, Alzheimer's disease, Parkinson's disease, Huntington's disease and amyotrophic lateral sclerosis, nerve pathological changes associated with acquired immunodeficiency, cerebrospinal multiple sclerosis, apoplexy or brain injury associated with physical stimulation, various neurodegenerative diseases affecting central or nervous system, cerebellum-brain stem atrophy, progressive ataxia syndrome, muscular dystrophy, progressive muscular atrophy, progressive bulbar inherited muscular atrophy, physical or traumatic injury of central or peripheral nervous system, prolapsed intervertebral disk syndrome, cervical spondylosis, thoracic outlet destruction syndromes, nerve plexus disorders, thoracic brachial plexus syndrome, various peripheral nerve pathological changes, trigeminal neuralgia, glossopharyngeal neuralgia, facial paralysis, various autoimmune disease which may cause injury of central or peripheral nervous system, myasthenia gravis, Guillain-Barre syndrome, dapsone ticks, bulbar and postbulbar optic nerve pathological changes, retinopathy, postbulbar optic neuritis, audition disorders, or tinnitus.

Among other things, the preferred neurological disorders include, but are not limited to, neurological disorders associated with neurodegeneration such as Alzheimer's disease, Parkinson's disease and amyotrophic lateral sclerosis, and neurological disorders associated with peripheral nerve pathological changes, which usually are caused by physical injuries brain or spinal cord or other associated diseases.

According to the invention, the compound of the present invention may be administered orally, by inhalation spray, rectally, nasally, buccally, vaginally, topically, parenterally (such as, subcutaneous, intravenous, intramuscular, intraperitoneal, intrachecal, intraventricular, intrasteral, and intracranial injection or infusion techniques), or via an implanted reservoir, preferably orally, intraperitoneally, or intravenously. In addition, in order to treat central nervous system disorders effectively, the compound of the present invention is preferably administered intraventricularly to overcome possible low blood-brain barrier penetration of the compound.

When administered orally, the compound of the invention may be produced in any orally acceptable formulation forms comprising, but being not limited to, tablets, capsules, aqueous solutions or aqueous suspensions. Typically, the carriers used for tablets comprises lactose and corn starch. In addition, lubricating agents such as magnesium stearate may also be added. Usually, the diluents used for capsules comprise lactose and dried corn starch. Aqueous suspension formulations generally comprise mixture of suitable emulsifying and suspending agents with the active ingredient. If desired, the oral formulation forms may further comprise sweetening agents, flavoring agents or coloring agents.

The compounds of the invention may also be administered rectally in the form of suppositories. These compositions can be prepared by mixing the drug with a suitable non-irritating excipient which is solid at room temperature, but liquid at rectal temperature and, therefore, will melt in the rectum to release the drug. Such materials include cocoa butter, beeswax and polyethylene glycols.

The compounds of this invention may also be administered topically, especially when the conditions addressed for treatment involve areas or organs readily accessible by topical application, including neurological disorders of the eye, the skin, or the lower intestinal tract. The compounds of the invention may be prepared into different topical administration formulations in accordance with the areas or organs.

For topical application to eyes, the compounds of the invention can be formulated as micronized suspensions or solutions in isotonic, pH adjusted sterile saline, either with or without a preservative such as benzylalkonium chloride. Alternatively, for the ophthalmic uses, the compounds may be formulated in an ointment such as petrolatum.

For topical application to the skin, the compounds can be formulated in a suitable ointment, lotion or cream wherein the active ingredient suspends or dissolves in one or more carriers. For example, the carriers suitable for ointment comprise mineral oil, liquid petrolatum, white petrolatum, propylene glycol, polyoxyethylene, polyoxypropylene, emulsifying wax and water; and the carriers suitable for lotion or cream comprise mineral oil, sorbitan monostearate, Tween 60, cetyl ester wax, cetearyl alcohol, 2-octyldodecanol, benzyl alcohol and water.

Topical application for the lower intestinal tract can be effected in a rectal suppository formulation (see above) or in a suitable enema formulation.

The compounds of the present invention may be administered in the form of sterile injectable preparations, for example, as sterile injectable aqueous or oleaginous suspensions. Among the acceptable carriers and solvents that may be employed are water, Ringer's solution and isotonic sodium chloride solution. In addition, sterile, fixed oils, such as mono- or di-glycerides, can be also employed as solvents or suspending mediums.

The compounds can be administered together with other neurotrophic substances such as neurotrophic growth factor (NGF), insulin growth factor (IGF-1), and derived growth factor thereof (gIGF-1), brain derived growth factor (BDGF), glial derived growth factor (GDGF), platelet derived growth factor (PDGF), fibroblast growth factor (aFGF and bFGF), ciliary neurotrophic factor (CNTF), neurotropin-3 (NT-3), and neurotropin-4/5 (NT-4/5), preferably NGF. Such two active ingredients may stimulate the growth of nerve synergistically.

It is understood, however, that a specific dose level for any particular patient will depend upon a variety of factors including the activity of the specific compound employed, the age, body weight, general health, sex, diet, time of administration, rate of excretion, drug combination, and the severity of the particular disease being treated and form of administration. Dosage levels on the order of about 0.01 mg to about 100 mg of the active ingredient/kg body weight/day are preferred.

The compounds of the present invention were synthesized through the following route:

Scheme:

wherein, Z=O or NH.

The method of the present invention is illustrated as following:

Compound 2 can be obtained by dissolving compound 1 (cysteine, available from ACROS) in a polar solvent (such as water or methanol), and adjusting pH to 7, and then adding epoxy ethane dropwise at a temperature of 0-10° C.;

Compound 3 can be obtained by dissolving compound 2 into concentrated hydrochloric acid and then stirring at 90-95° C.;

Compound 4 can be obtained by dissolving compound 3 in a suitable amount of methanol, and passing dry hydrogen chloride gas in the solution;

Compound 5 can be obtained by dissolving compound 4 in a polar non-protonic solvent (such as DMF) in the presence of bases at 90-95° C. to give a free amine and then reacting with the solution of HCl in ethyl ether or ethanol;

Compound 6 can be obtained by dissolving compound 5 in $CH_2Cl_2$ or THF at 0° C. and reacting with the solution of $R_1SO_2Cl$ and triethyl amine in $CH_2Cl_2$ at room temperature.;

Compound 7 can be obtained by dissolving compound 6 in methanol at 0° C. and reacting with alkali metal hydroxide such as LiOH at room temperature;

Compound 8 can be obtained by reacting compound 7, $R_2OH$, or $R_2NH_2$, DCC, DMAP, TEA in $CH_2Cl_2$ or THF at room temperature; and Compound 9 can be obtained by oxidizing compound 8 with MCPBA in $CH_2Cl_2$ or THF.

EXAMPLES

The following examples are preferred illustrative examples of the invention and these preferred examples do not intend to limit the present invention.

Example 1

Synthesis of 2-{[(3R)-4-(4-toluenesulfonyl)thiomorpholine-3-carbonyl]amino}-3-phenyl-propionic acid benzyl ester 2-amino-3-(2-hydroxy-ethylsulfanyl)-propionic acid 36.3 g of L-cysteine was dissolved in 300 ml of water. 24 ml 1 mol/L of NaOH solution was added into above solution and cooled by ice-water bath in order to adjust pH value to 7. And then at 0° C. 30 mL of epoxy ethane was added dropwise to the above solution and then mixture was cooled to 10° C. After the mixture was stirred for 1.0 hour, it was warmed to room temperature and then stirred for 1.5 hours. The resultant mixture was extracted with ethyl ether three times (60 ml, 45 ml, 45 ml) to remove the residual epoxy ethane. Water layer was removed on a rot-vap to obtain a buff solid. The solid was recrystallized in 95% ethanol to obtain a white lamellar crystal (33.9 g). Yield 69.4%□mp 195-196° C. (Dec.).

$^1$H-NMR (400 MHz, $D_2O$): δ 3.96131 (dd, 1H, $J_1$=4.272 Hz, $J_2$=7.816 Hz), 3.80680-3.77293 (m, 2H), 3.17887 (dd, 1H, $J_1$=4.268 Hz, $J_2$=14.814 Hz), 3.08224 (dd, 1H, $J_1$=7.480 Hz, $J_2$=14.814 Hz), 2.80103 (t, 2H, J=6.036 Hz).

2-Amino-3-(2-chloro-ethylsulfanyl)-propionic acid hydrochloride 33.9 g of 2-amino-3-(2-hydroxy-ethylsulfanyl)-propionic acid was dissolved in 800 mL of concentrated hydrogen chloride and the solution was stirred for 7 h to obtain a buff solid. The solid was recrystallized in isopropanol to obtain a white powder (34.2 g). Yield 75.4%, mp 185-186° C.

$^1$H-NMR (400 MHz, $D_2O$): δ 6 4.30477-4.26952 (m, 1H), 3.81913-3.78409 (m, 2H), 3.25903 (dd, 1H, $J_1$=4.444 Hz, $J_2$=14.984 Hz), 3.18877 (dd, 1H, $J_1$32 7.352 Hz, $J_2$=15.072 Hz), 3.04410-3.00625 (m, 2H).

2-Amino-3-(2-chloro-ethylsulfanyl)-propionic acid methyl ester hydrochloride 34.2 g of 2-amino-3-(2-chloro-ethylsulfanyl)-propionic acid hydrochloride was dissolved in 300 mL of absolute methanol (treated with Mg) and dry HCl gas (prepared from 250 ml of concentrated sulfuric acid and 200 g of ammonium chloride) was put in the above solution till saturation. And then the mixture was stirred for 12 hour and methanol was removed to obtain 36.3 g white solid. Yield 100%, mp 128-129° C.

$^1$H-NMR (400 MHz, $D_2O$): δ 4.45277 (dd, 1H, $J_1$=4.504 Hz, $J_2$=7.484 Hz), 3.89729 (s, 3), 3.81650-3.77860 (tm, 2H), 3.33808 (dd, 1H, $J_1$=4.480 Hz, $J_2$=15.034 Hz), 3.19579 (dd, 1H, $J_1$=7.500 Hz, $J_2$=14.992 Hz), 3.04047-2.98506 (m, 2H).

(3R)-thiomorpholine-3-carboxylic acid methyl ester 36.3 g of 2-amino-3-(2-chloro-ethylsulfanyl)-propionic acid methyl ester hydrochloride was dissolved in 700 mL of dry DMF in a 100 ml three neck flask and 125 mL of TEA was added dropwise into the above solution. And then the mixture was stirred for 8 hours at 90-95° C. The white solid was removed and the mother liquid was concentrated to obtain a red oil (10.9 g). The obtained red oil was dissolved in ethyl acetate and washed with saturated aqueous sodium chloride solution (50, 40, 40 ml) and then with water (40 ml) and dried over $MgSO_4$. The drying agent and ethyl acetate were removed to obtain a brown oil (10.9 g). Yield 43.6%.

(3R)-thiomorpholine-3-carboxylic acid methyl ester hydrochloride 10.9 g of (3R)-thiomorpholine-3-carboxylic acid methyl ester was dissolved in 150 mL of ether and 90 mL 14.5% of hydrogen chloride dissolved in ethanol was added dropwise in the above solution to obtain 13.0 g of (3R)-thiomorpholine-3-carboxylic acid methyl ester hydrochloride as a white solid. Yield 97.2%□mp 160-161° C.

$^1$H-NMR (400 MHz, DMSO):δ 10.0898 (brs, 2H),4.4214 (dd, 1H, $J_1$=3.52 Hz, $J_2$=8.56 Hz), 3.7833 (s, 3H), 3.4986-3.4766 (m, 1H), 3.2246-3.0606 (m, 3H), 2.9897-2.9593 (m, 1H), 2.8763-2.8622 (m, 1H); MS (FAB) m/z: 162.0 (M-35.5), 102.0,74.0.

(3R)-4-(4-toluenesulfonyl)thiomorpholine-3-carboxylic acid methyl ester 13.0 g of (3R)-thiomorpholine-3-carboxylic acid methyl ester hydrochloride was dissolved in 120 mL of methylene chloride and 30 mL of triethylamine was added dropwise in the above mixture. After stirring for 1 h, 13.5 g of p-toluenesulfonyl chloride dissolved in 120 mL of methylene chloride was added dropwise into the solution and stirred for 24 h at room temperature. The white solid appeared in the process of reaction was removed by filtration and the mother liquid was washed with saturated NaHCO$_3$ and water and dried with Na$_2$SO$_4$ overnight. After filtrating and collecting of mother liquid, solvent was distilled and a white solid was obtained. The solid was recrystallized from ethyl acetate and cyclohexane to obtain 19.4 g product as a white crystal. Yield 93.5%□mp 87-88° C.□$[α]_D^{24.5}$=−78.1° (2.00 g/100 ml, CH$_2$Cl$_2$).

$^1$H-NMR (400 MHz, CDCl$_3$): δ 7.66938(d, 2H, J=7.352 Hz), 7.29941(d, 2H, J=8.036 Hz), 5.06654 (t, 1H, J=3.436 Hz), 4.04908-3.99999 (m, 1H), 3.63087 (s, 3H), 3.45333-3.38197 (m, 1H), 3.06102-3.02157 (m, 1H), 3.00305-2.95904 (m, 1H), 2.82287-2.74967 (m, 1H), 2.42975 (s, 3H), 2.40451-2.36514(1H).

(3R)-4-(4-toluenesulfonyl)thiomorpholine-3-carboxylic acid 8.3 g of (3R)-4-(4-toluenesulfonyl)thiomorpholine-3-carboxylic acid methyl ester was dissolved in 157 mL of methanol and 52.5 ml 1 mol/L of LiOH solution was added dropwise in the above solution at 0° C. The mixture was stirred for 48 h and ethyl acetate (60, 60 ml) was added into the reaction mixture and separated to collect mother liquid. The mother liquid was acidified by 100 ml 1 mol/L hydrogen chloride to adjust pH value to 2. Filtrated and collected the white solid to obtain 7.7 g product. Yield 97.0%□mp149-150° C.

$^1$H-NMR (400 MHz, CDCl$_3$): δ 9.87650 (brs, 1H), 7.68301-7.65750 (m, 2H), 7.29537(d, 2H, J=8.024 Hz), 5.11555 (t, 1H, J=3.456 Hz), 4.04252-3.99349 (m, 1H), 3.47279-3.40112 (m, 1H), 3.06220-2.96007 (m, 2H), 2.80470-2.73149 (m, 1H), 2.42613 (s, 3H), 2.38398 (s, 1H).

2-{[(3R)-4-(4-toluenesulfonyl)thiomorpholine-3-carbonyl]amino}-3-phenyl-propionic acid benzyl ester 0.602 g (2 mmol) of (3R)-4-(4-toluenesulfonyl)thiomorpholine-3-carboxylic acid, 0.939 g (2.2 mmol) of L-phenylalanine benzyl ester p-toluenesulfonic acid salt, 0.454 g (2.2 mmol) of DCC and 0.224 g (2 mmol) of DMAP were dissolved in 30 mL of CH$_2$Cl$_2$, 0.4 ml (2.7 mmol) of TEA was added. The mixture was stirred for 24 h at room temperature. The solid was filtrated and the solvent was evaporated. The residual was dissolved in a suitable amount of ethyl acetate (20 ml) and then the mixture was filtered to remove insoluble substance. The ethyl acetate was added to 60 ml and then the liquid was washed with 10% NaHCO$_3$ solution, saturated NaCl solution and dried over Na$_2$SO$_4$. After the drying agent was removed and part of ethyl acetate was evaporated, the crude product was purified by flash column chromatography (eluent: CH$_2$Cl$_2$:CH$_3$Cl=1:1) to obtain the product as a glassy solid (0.80 g).

$^1$H-NMR (400 MHz, CDCl$_3$): δ 7.66072-7.63134 (m, 2H), 7.37633-7.34761 (m, 4H), 7.30475-7.28315 (m, 4H), 7.25816-7.18850 (m, 2H), 7.08602-7.06666 (m, 2H), 6.92373(d, 0.5H, J=7.092 Hz), 6.83414(d, 0.5H, J=7.092 Hz), 5.23479(d, 0.5H, J=12.148 Hz), 5.16985 (dd, 1H, $J_1$=4.796 Hz, 4.956 Hz, $J_2$=12.108 Hz), 5.07028(d, 0.5H, J=12.000 Hz), 498245-4.96101 (m, 0.5H), 4.84773-4.83241 (m, 0.5H), 4.77844-4.71409 (m, 1H), 3.95856-3.89722 (m, 1H), 3.30404 (dd, 0.5H, $J_1$=5.772 Hz, 5.752 Hz, $J_2$=13.994 Hz), 3.22070-3.01464 (m, 3H), 2.79171-2.71763 (m, 0.5H), 2.54595-2.50159 (m, 0.5H), 2.46259-2.39754 (m, 4H), 2.32092 (brs, 0.5H), 2.05599-1.94058 (m, 1H); MS (EI) m/z: 539.1, 383.0, 283.9, 255.9, 190.0, 154.9, 120.0, 91.0, 65.0.

Example 2

Synthesis of 2-{[(3R)-4-(4-toluenesulfonyl)thiomorpholine-3-carbonyl]amino}-3-methyl-butyric acid benzyl ester 0.301 g (1 mmol) of (3R)-4-(4-toluenesulfonyl)thiomorpholine-3-carboxylic acid, 0.417 g (1.1 mmol) of L-valine benzyl ester p-toluenesulfonic acid salt, 0.227 g (1.2 mmol) of DCC and 0.122 g (1 mmol) of DMAP were dissolved in 30 mL of CH$_2$Cl$_2$, 0.2 ml (1.4 mmol) of TEA was added. The mixture was stirred for 24 h at room temperature. The solid was filtrated and the solvent was evaporated. The residual was dissolved in a suitable amount of ethyl acetate (20 ml) and then the mixture was filtered to remove insoluble substance. The ethyl acetate was added to 60 ml and then the liquid was washed with 10% NaHCO$_3$ solution, saturated NaCl solution and dried over Na$_2$SO$_4$. After the drying agent was removed and part of ethyl acetate was evaporated, the crude product was purified by flash column chromatography (eluent: CH$_2$Cl$_2$:CH$_3$Cl=1:1) to obtain the product as a glassy solid (0.20 g).

$^1$H-NMR (400 MHz, CDCl$_3$): δ 7.7688-7.7235 (m, 2H), 7.3730-7.3271 (m, 7H), 6.9956(d, 0.5H, J=9.16 Hz), 6.9125 (d, 0.5H, J=9.16 Hz), 5.2509-5.2109 (m, 1H), 5.1697 (m, 1H), 4.7891 (brs, 1H), 4.6640 (dd, 0.5H, $J_1$=4.44 Hz, 4.47 Hz, $J_2$=9.19 Hz), 4.5986 (dd, 0.5H, $J_1$=4.58 Hz, $J_2$=8.59 Hz), 4.2220(d, 0.5H, J=14.68 Hz), 4.0949(d, 0.5H, J=14.78 Hz), 3.4084-3.2968 (m, 1H), 3.1353(d, 1H, J=12.23 Hz), 5.2997-2.3978 (m, 5H), 2.2581-2.0801 (m, 2H), 0.9311 (dd, 3H, $J_1$=6.84 Hz, 6.86 Hz, $J_2$=17.51 Hz), 0.8297 (dd, 3H, $J_1$=6.98 Hz, 6.94 Hz, $J_2$=6.73 Hz); MS (EI) m/z: 491.1, 355.0, 335.0, 255.9, 190.0, 154.9, 138.9, 91.0, 65.0.

Example 3

Synthesis of 2-{[(3R)-4-(4-toluenesulfonyl)thiomorpholine-3-carbonyl]amino}-4-methyl-pentanoic acid benzyl ester 0.301 g (1 mmol) of (3R)-4-(4-toluenesulfonyl)thiomorpholine-3-carboxylic acid, 0.432 g (1.1 mmol) of L-leucine benzyl ester p-toluenesulfonic acid salt, 0.227 g (1.2 mmol) of DCC and 0.122 g (1 mmol) of DMAP were dissolved in 30 mL of CH$_2$Cl$_2$, 0.2 ml (1.4 mmol) of TEA was added. The mixture was stirred for 24 h at room temperature. The solid was filtrated and the solvent was evaporated. The residual was dissolved in a suitable amount of ethyl acetate (20 ml) and then the mixture was filtered to remove insoluble substance. The ethyl acetate was added to 60 ml and then the liquid was washed with 10% NaHCO$_3$ solution, saturated NaCl solution and dried over Na$_2$SO$_4$. After the drying agent was removed and part of ethyl acetate was evaporated, the crude product was purified by flash column chromatography (eluent: CH$_2$Cl$_2$:CH$_3$Cl=1:1) to obtain the product as a oil (0.48 g).

$^1$H-NMR (400 MHz, CDCl$_3$): δ 7.7222(d, 2H, J=8.20 Hz), 7.3910-7.3366 (m, 7H), 6.7213(d, 1H, J=8.80 Hz), 5.2003(d, 1H, J=12.16 Hz), 5.0994(d, 1H, J=12.16 Hz), 4.7786-4.7329 (m, 2H), 4.1188(d, 1H, J=14.80 Hz), 3.4060-3.3329 (m, 1H), 3.1096(d, 1H, J=13.64 Hz), 2.5188-2.3676 (m, 5H), 2.0538(d, 1H, J=13.44 Hz), 1.6967-1.4486 (m, 3H), 0.9175 (d, 3H, J=2.49 Hz), 0.9018 (d, 3H, J=2.53 Hz); MS (EI) m/z: 505.4, 368.8, 348.8, 283.9, 255.9, 190.0, 155.0, 112.0, 90.0, 65.0.

Example 4

Synthesis of 2-{[(3R)-4-(4-toluenesulfonyl)thiomorpholine-3-carbonyl]amino}-4-methyl-pentanoic acid ethyl ester 0.301 g (1 mmol) of (3R)-4-(4-toluenesulfonyl)thiomorpholine-3-carboxylic acid, 0.215 g (1.1 mmol) of L-leucine ethyl ester hydrochlorid, 0.227 g (1.2 mmol) of DCC and 0.122 g (1 mmol) of DMAP were dissolved in 30 mL of CH$_2$Cl$_2$, 0.2 ml (1.4 mmol) of TEA was added. The mixture was stirred for 24 h at room temperature. The solid was filtrated and the solvent was evaporated. The residual was dissolved in a suitable amount of ethyl acetate (20 ml) and then the mixture was filtered to remove insoluble substance. The ethyl acetate was added to 60 ml and then the liquid was washed with 10% NaHCO$_3$ solution, saturated NaCl solution and dried over Na$_2$SO$_4$. After the drying agent was removed and part of ethyl acetate was evaporated, the crude product was purified by flash column chromatography (eluent: CH$_2$Cl$_2$:CH$_3$Cl=1:1) to obtain the product as a oil (0.36 g).

$^1$H-NMR (400 MHz, CDCl$_3$): δ 7.77237-7.74077 (m, 2H), 7.36382(d, 2H, J=7.988 Hz), 6.74090(d, 1H, J=9.244 Hz), 4.80098-4.77466 (m, 1H), 4.68244-4.58898 (m, 1H), 4.28174-4.15708 (m, 3H), 3.53789-3.28674 (m, 1H), 3.13092 (d, 1H, J=13.676), 2.56954-2.42247 (m, 5H), 2.24620-2.20545 (m, 1H), 1.66352-1.53450 (m, 3H), 1.30702-1.26745 (m, 3H), 0.96159-0.91891 (m, 6H); MS (EI) m/z: 443.1, 397.1, 369.1, 287.1, 256.0, 213.1,155.0, 139.0, 112.0, 91.0, 65.0.

Example 5

Synthesis of (3R)-4-(4-toluenesulfonyl)thiomorpholine-3-carboxylic acid [3-(pyridin-3-yl)]-propyl ester 0.301 g (1 mmol) of (3R)-4-(4-toluenesulfonyl)thiomorpholine-3-carboxylic acid, 0.206 g (1.5 mmol) of 3-(pyridin-3-yl)-propanol, 0.088 g (0.33 mmol) of CAS, 0.227 g (1.2 mmol) of DCC and 0.04 g (0.33 mmol) of DMAP were dissolved in 15 mL of CH$_2$Cl$_2$. The mixture was stirred for 24 h at room temperature. The solid was filtrated and the solvent was evaporated. The residual was dissolved in a suitable amount of ethyl acetate (20 ml) and then the mixture was filtered to remove insoluble substance. The ethyl acetate was added to 60 ml and then the liquid was washed with 10% NaHCO$_3$ solution, saturated NaCl solution and dried over Na$_2$SO$_4$. After the drying agent was removed and part of ethyl acetate was evaporated, the crude product was purified by flash column chromatography (eluent: ethyl acetate:cyclohexane=1:1) to obtain the product as a oil (0.39 g).

$^1$H-NMR (400 MHz, CDCl$_3$): δ 8.4699-8.4438 (m, 2H), 7.6702(d, 2H, J=8.24 Hz), 7.5056-7.4863 (m, 1H), 7.2847-7.2140 (m, 3H), 5.0708 (t, 1H, J=3.35 Hz), 4.1237-4.0851 (m, 2H), 4.0284-3.9869 (m, 1H), 3.4732-3.4018 (m, 1H), 3.0225-2.9603 (m, 2H), 2.8096-2.7364 (m, 1H), 2.6714-2.6327 (m, 2H), 2.4134-2.3756 (m, 4H), 1.9315-1.8778 (m, 2H); MS (EI) m/z: 421.8, 347.3, 265.4, 237.3, 192.3, 155.2, 119.9, 90.9, 64.9.

Example 6

Synthesis of (3R)-4-(4-toluenesulfonyl)thiomorpholine-3-carboxylic acid [N-methyl-N-(pyridin-2-yl)]-ethyl ester 0.301 g (1 mmol) of (3R)-4-(4-toluenesulfonyl)thiomorpholine-3-carboxylic acid, 0.228 g (1.5 mmol) of N-methyl-N-(pyridin-2-yl)-ethanol, 0.088 g (0.33 mmol) of CAS, 0.227 g (1.2 mmol) of DCC and 0.04 g (0.33 mmol) of DMAP were dissolved in 15 mL of CH$_2$Cl$_2$. The mixture was stirred for 24 h at room temperature. The solid was filtrated and the solvent was evaporated. The residual was dissolved in a suitable amount of ethyl acetate (20 ml) and then the mixture was filtered to remove insoluble substance. The ethyl acetate was added to 60 ml and then the liquid was washed with 10% NaHCO$_3$ solution, saturated NaCl solution and dried over Na$_2$SO$_4$. After the drying agent was removed and part of ethyl acetate was evaporated, the crude product was purified by flash column chromatography (eluent: ethyl acetate:cyclohexane=1:1) to obtain the product as a oil (0.32 g).

$^1$H-NMR (400 MHz, CDCl$_3$): δ 8.15202-8.13465 (m, 1H), 7.65765-7.63191 (m, 2H), 7.48462-7.44059 (m, 1H), 7.27137-7.25120 (m, 2H), 6.57550 (dd, 1H, J$_1$=5.088 Hz, 5.352 Hz, J$_2$=6.864 Hz), 6.49163(d, 1H, J=8.564 Hz), 5.00609 (t, 1H, J=3.348 Hz), 4.31854-4.21503 (m, 2H), 3.99180-3.95109 (m, 1H), 3.89777-3.84669 (m, 1H), 3.77810-3.72768 (m, 1H), 3.42992-3.35844 (m, 1H), 3.03108 (s, 3H), 2.91483(d, 2H, J=3.640 Hz), 2.77988-2.70670 (m, 1H), 2.40416 (s, 3H), 2.34020-2.30628 (m, 1H); MS (EI) m/z: 435.0, 280.0, 256.0, 154.9, 135.0, 121.0, 107.0, 91.0, 65.0.

Example 7

Synthesis of (3R)-4-(4-toluenesulfonyl)thiomorpholine-3-carboxylic acid phenylpropyl ester 0.301 g (1 mmol) of (3R)-4-(4-toluenesulfonyl)thiomorpholine-3-carboxylic acid, 0.204 g (1.5 mmol) of phenylpropanol, 0.088 g (0.33 mmol) of CAS, 0.227 g (1.2 mmol) of DCC and 0.04 g (0.33 mmol) of DMAP were dissolved in 15 mL of CH$_2$Cl$_2$. The mixture was stirred for 24 h at room temperature. The solid was filtrated and the solvent was evaporated. The residual was dissolved in a suitable amount of ethyl acetate (20 ml) and then the mixture was filtered to remove insoluble substance. The ethyl acetate was added to 60 ml and then the liquid was washed with 10% NaHCO$_3$ solution, saturated NaCl solution and dried over Na$_2$SO$_4$. After the drying agent was removed and part of ethyl acetate was evaporated, the crude product was purified by flash column chromatography (eluent: ethyl acetate: cyclohexane=2:1) to obtain the product as an oil (0.27 g).

$^1$H-NMR (400 MHz, CDCl$_3$): δ 7.67345(d, 2H, J=8.324 Hz), 7.31068-7.26240 (m, 4H), 7.22238-7.18556 (m, 1H), 7.16516 (m, 2H), 5.06053 (t, 1H, J=3.408 Hz), 4.10609-4.00046 (m, 3H), 3.48604-3.41471 (m, 1H), 3.02055-3.00423 (m, 2H), 2.83838-2.76520 (m, 1H), 2.63293 (t, 2H, J=7.452 Hz), 2.41556-2.38244 (m, 4H), 1.91367-1.84295 (m, 2H); MS (EI) m/z: 419.5, 300.5, 255.4, 154.6, 138.7, 116.8, 90.8, 64.9.

Example 8

Synthesis of (3R)-4-(4-toluenesulfonyl)thiomorpholine-3-carboxylic acid (2-trifluoromethyl)-phenylethyl ester 0.301 g (1 mmol) of (3R)-4-(4-toluenesulfonyl)thiomorpholine-3-carboxylic acid, 0.285 g (1.5 mmol) of (2-trifluoromethyl)-phenylethanol, 0.088 g (0.33 mmol) of CAS, 0.227 g (1.2 mmol) of DCC and 0.04 g (0.33 mmol) of DMAP were dissolved in 15 mL of CH$_2$Cl$_2$. The mixture was stirred for 24 h at room temperature. The solid was filtrated and the solvent was evaporated. The residual was dissolved in a suitable amount of ethyl acetate (20 ml) and then the mixture was filtered to remove insoluble substance. The ethyl acetate was added to 60 ml and then the liquid was washed with 10% NaHCO$_3$ solution, saturated NaCl solution and dried over Na$_2$SO$_4$. After the drying agent was removed and part of ethyl acetate was evaporated, the crude product was purified by flash column chromatography (eluent: ethyl acetate:cyclohexane=1:3) to obtain the product as a oil (0.44 g).

$^1$H-NMR (400 MHz, CDCl$_3$): δ 7.6631-7.6316 (m, 3H), 7.5113-7.4740 (m, 1H), 7.3733-7.2847 (m, 4H), 5.0451 (t, 1H, J=3.38 Hz), 4.3385-4.2132 (m, 2H), 4.0266-3.99777 (m, 1H), 3.4194-3.3481 (m, 1H), 3.0712-3.0357 (m, 2H), 2.9794-2.9707 (m, 2H), 2.8070-2.7340 (m, 1H), 2.4153 (s, 3H), 2.3575(d, 1H, J=13.59 Hz); MS (EI) m/z: 472.9, 399.9, 317.9, 255.8, 172.9, 154.9, 132.9, 117.9, 100.9, 64.9.

Example 9

Synthesis of (3R)-4-(4-toluenesulfonyl)thiomorpholine-3-carboxylic acid (N-methyl-N-benzyl)-ethyl ester 0.301 g (1 mmol) of (3R)-4-(4-toluenesulfonyl)thiomorpholine-3-carboxylic acid, 0.275 g (1.5 mmol) of (N-methyl-N-benzyl)-ethanol, 0.088 g (0.33 mmol) of CAS, 0.227 g (1.2 mmol) of DCC and 0.04 g (0.33 mmol) of DMAP were dissolved in 15 mL of CH$_2$Cl$_2$. The mixture was stirred for 24 h at room temperature. The solid was filtrated and the solvent was evaporated. The residual was dissolved in a suitable amount of ethyl acetate (20 ml) and then the mixture was filtered to remove insoluble substance. The ethyl acetate was added to 60 ml and then the liquid was washed with 10% NaHCO$_3$ solution, saturated NaCl solution and dried over Na$_2$SO$_4$. After the drying agent was removed and part of ethyl acetate was evaporated, the crude product was purified by flash column chromatography (eluent: ethyl acetate:cyclohexane=1:2) to obtain the product as a oil (0.36 g).

$^1$H-NMR (400 MHz, CDCl$_3$): δ 7.6627-7.6418 (m, 2H), 7.3460-7.2454 (m, 7H), 5.0666 (t, 1H, J=3.40 Hz), 4.2701-4.2416 (m, 2H), 4.0184-3.9844 (m, 1H), 3.5281-3.4331 (m, 3H), 3.0252-2.9927 (m, 2H), 2.7929-2.7614 (m, 1H), 2.5949 (brs, 2H), 2.4087-2.3563 (m, 4H), 2.2302 (s, 3H); MS (EI) m/z: 449.4, 292.9, 255.9, 154.9, 133.8, 90.9, 64.9.

Example 10

Synthesis of (3R)-4-(4-toluenesulfonyl)thiomorpholine-3-carboxylic acid (3-phenyl)-allyl ester 0.301 g (1 mmol) of (3R)-4-(4-toluenesulfonyl)thiomorpholine-3-carboxylic acid, 0.200 g (1.5 mmol) of (3-phenyl)-allyl alcohol, 0.088 g (0.33 mmol) of CAS, 0.227 g (1.2 mmol) of DCC and 0.04 g (0.33 mmol) of DMAP were dissolved in 15 mL of CH$_2$Cl$_2$. The mixture was stirred for 24 h at room temperature. The solid was filtered and the solvent was evaporated. The residual was dissolved in a suitable amount of ethyl acetate (20 ml) and then the mixture was filtered to remove insoluble substance. The ethyl acetate was added to 60 ml and then the liquid was washed with 10% NaHCO$_3$ solution, saturated NaCl solution and dried over Na$_2$SO$_4$. After the drying agent was removed and part of ethyl acetate was evaporated, the crude product was purified by flash column chromatography (eluent: ethyl acetate:cyclohexane=1:4) to obtain the product as a oil (0.21 g).

$^1$H-NMR (400MHz, CDCl$_3$): δ 7.6671(d, 2H, J=8.32 Hz), 7.3832-7.2378 (m, 7H), 6.5952(d, 1H, J=15.88 Hz), 6.1464-6.1066 (m, 1H), 5.1104 (t, 1H, J=3.39 Hz), 4.7680-4.7170 (m, 1H), 4.6815-4.6336 (m, 1H), 4.0600-4.0113 (m, 1H), 3.4935-3.4223 (m, 1H), 3.1124-3.0724 (m, 1H), 3.0388-2.9948 (m, 1H), 2.8503-2.7772 (m, 1H), 2.4238-2.3707 (m, 4H); MS (EI) m/z: 417.0, 299.9, 255.9, 154.9, 134.0, 117.0, 108.0, 91.0, 65.0.

Example 11

Synthesis of (3R)-4-(4-toluenesulfonyl)thiomorpholine-3-carboxylic acid (3-cyclohexyl)-propyl ester, 0.301 g (1 mmol) of (3R)-4-(4-toluenesulfonyl)thiomorpholine-3-carboxylic acid, 0.213 g (1.5 mmol) of (3-cyclohexyl)-propanol, 0.088 g (0.33 mmol) of CAS, 0.227 g (1.2 mmol) of DCC and 0.04 g (0.33 mmol) of DMAP were dissolved in 15 mL of CH$_2$Cl$_2$. The mixture was stirred for 24 h at room temperature. The solid was filtrated and the solvent was evaporated. The residual was dissolved in a suitable amount of ethyl acetate (20 ml) and then the mixture was filtered to remove insoluble substance. The ethyl acetate was added to 60 ml and then the liquid was washed with 10% NaHCO$_3$ solution, saturated NaCl solution and dried over Na$_2$SO$_4$. After the drying agent was removed and part of ethyl acetate was evaporated, the crude product was purified by flash column chromatography (eluent: ethyl acetate:cyclohexane=1:4) to obtain the product as a oil (0.33 g).

$^1$H-NMR (400 MHz, CDCl$_3$): δ 7.6705(d, 2H, J=8.28 Hz), 7.2869(d, 2H, J=8.40 Hz), 5.0506 (t, 1H, J=3.38 Hz), 4.0627-3.9712 (m, 3H), 3.4698-3.3986 (m, 1H), 3.0360-3.0058 (m, 2H), 2.8073-2.7996 (m, 1H), 2.4237-2.3733 (m, 4H),1.7151-1.6566 (m, 5H), 1.5460-1.5076 (m, 2H), 1.2338-1.1368 (m, 6H), 0.8684-0.8380 (m, 2H); MS (EI) m/z: 425.9, 301.8, 269.9, 255.8, 154.8, 102.9, 90.9, 69.0.

Example 12

Synthesis of (3R)-4-(4-toluenesulfonyl)thiomorpholine-3-carboxylic acid (1,3-diphenyl)-propyl ester 0.301 g (1 mmol) of (3R)-4-(4-toluenesulfonyl)thiomorpholine-3-carboxylic acid, 0.318 g (1.5 mmol) of (1,3- diphenyl)-propanol, 0.088 g (0.33 mmol) of CAS, 0.227 g (1.2 mmol) of DCC and 0.04 g (0.33 mmol) of DMAP were dissolved in 15 mL of $CH_2Cl_2$. The mixture was stirred for 24 h at room temperature. The solid was filtrated and the solvent was evaporated. The residual was dissolved in a suitable amount of ethyl acetate (20 ml) and then the mixture was filtered to remove insoluble substance. The ethyl acetate was added to 60 ml and then the liquid was washed with 10% $NaHCO_3$ solution, saturated NaCl solution and dried over $Na_2SO_4$. After the drying agent was removed and part of ethyl acetate was evaporated, the crude product was purified by flash column chromatography (eluent: ethyl acetate:cyclohexane=1:3) to obtain the product as a oil (0.15 g). $^1$H-NMR (400 MHz, $CDCl_3$): δ 7.5040(d, 2H, J=8.32 Hz), 7.3751-7.0634 (m, 12H), 5.7186-5.6846 (m, 1H), 5.0645 (t, 1H, J=3.42 Hz), 4.0136-3.9800 (m, 1H), 3.4760-3.4052 (m, 1H), 3.1031-3.0773 (m, 2H), 2.8562-2.7914 (m, 1H), 2.6613-2.5414 (m, 2H), 2.4304-2.3855 (m, 1H), 2.3333 (s, 3H), 2.2283-2.2041 (m, 1H), 2.0565-2.0328 (m, 1H); MS (EI) m/z: 495.8, 449.8, 391.8, 339.8, 299.7, 255.7, 193.8, 154.8, 138.8, 116.9, 90.8, 64.9.

Example 13

Synthesis of (3R)-4-(4-toluenesulfonyl)thiomorpholine-3-carboxylic acid (1-p-methoxyphenyl-3-phenyl)-propyl ester 0.301 g (1 mmol) of (3R)-4-(4-toluenesulfonyl)thiomorpholine-3-carboxylic acid, 0.242 g (1.0 mmol) of (1-p-methoxyphenyl-3-phenyl)-propanol, 0.088 g (0.33 mmol) of CAS, 0.227 g (1.2 mmol) of DCC and 0.04 g (0.33 mmol) of DMAP were dissolved in 15 mL of $CH_2Cl_2$. The mixture was stirred for 24 h at room temperature. The solid was filtrated and the solvent was evaporated. The residual was dissolved in a suitable amount of ethyl acetate (20 ml) and then the mixture was filtered to remove insoluble substance. The ethyl acetate was added to 60 ml and then the liquid was washed with 10% $NaHCO_3$ solution, saturated NaCl solution and dried over $Na_2SO_4$. After the drying agent was removed and part of ethyl acetate was evaporated, the crude product was purified by flash column chromatography (eluent: ethyl acetate:cyclohexane=1:4) to obtain the product as a oil (0.20 g). $^1$H-NMR (400 MHz, $CDCl_3$): δ 7.5282(d, 2H, J=8.32 Hz), 7.2780-7.1066 (m, 9H), 6.8882(d, 2H, J=6.76 Hz), 5.6898-5.6552 (m, 1H), 5.0336 (t, 1H, J=6.69 Hz), 4.0021-3.9684 (m, 1H), 3.8409 (s, 3H), 3.4592-3.3883 (m, 1H), 3.0842-3.0182 (m, 2H), 2.8402-2.7839 (m, 1H), 2.6359-2.5973 (m, 1H), 2.5402-2.5160 (m, 1H), 2.4131-2.3527 (m, 4H), 2.2194-2.1947 (m, 1H), 2.0300-2.0048 (m, 1H); MS (EI) m/z: 525.6, 392.5, 301.5, 255.6, 224.6, 192.7, 177.7, 155.1,121.2, 90.8, 64.9.

Example 14

Synthesis of (3R)-4-(4-toluenesulfonyl)thiomorpholine-3-carboxylic acid (1-p-fluorophenyl-3-phenyl)-propyl ester 0.301 g (1 mmol) of (3R)-4-(4-toluenesulfonyl)thiomorpholine-3-carboxylic acid, 0.230 g (1.0 mmol) of (1-p-fluorophenyl-3-phenyl)-propanol, 0.088 g (0.33 mmol) of CAS, 0.227 g (1.2 mmol) of DCC and 0.04 g (0.33 mmol) of DMAP were dissolved in 15 mL of $CH_2Cl_2$. The mixture was stirred for 24 h at room temperature. The solid was filtrated and the solvent was evaporated. The residual was dissolved in a suitable amount of ethyl acetate (20 ml) and then the mixture was filtered to remove insoluble substance. The ethyl acetate was added to 60 ml and then the liquid was washed with 10% $NaHCO_3$ solution, saturated NaCl solution and dried over $Na_2SO_4$. After the drying agent was removed and part of ethyl acetate was evaporated, the crude product was purified by flash column chromatography (eluent: ethyl acetate:cyclohexane=1:4) to obtain the product as a oil (0.39 g).
$^1$H-NMR (400 MHz, $CDCl_3$): δ 7.6791-7.5152 (m, 2H), 7.2611-7.0466 (m, 11H), 5.6948-5.6605 (m, 1H), 5.0412 (t, 1H, J=3.41 Hz), 4.0181-3.9703 (m, 1H), 3.4608-3.3958 (m, 1H), 3.0823-3.0528 (m, 2H), 2.8056-2.7655 (m, 1H), 2.6484-2.6102 (m, 1H), 2.5565-2.5328 (m, 1H), 2.4185-2.3502 (m, 4H), 2.2235-2.1996 (m, 2H); MS (EI) m/z: 513.6, 468.5, 392.1, 358.4, 301.7, 255.6, 212.2, 180.8, 154.8, 109.1, 90.9, 64.9.

Example 15

Synthesis of (3R)-4-(4-toluenesulfonyl)thiomorpholine-3-carboxylic acid [3-phenyl-1-(thiophen-2-yl)]-propyl ester 0.301 g (1 mmol) of (3R)-4-(4-toluenesulfonyl)thiomorpholine-3-carboxylic acid, 0.218 g (1.0 mmol) of 3-phenyl-1-(thiophen-2-yl)-propanol, 0.088 g (0.33 mmol) of CAS, 0.227 g (1.2 mmol) of DCC and 0.04 g (0.33 mmol) of DMAP were dissolved in 15 mL of $CH_2Cl_2$. The mixture was stirred for 24 h at room temperature. The solid was filtrated and the solvent was evaporated. The residual was dissolved in a suitable amount of ethyl acetate (20 ml) and then the mixture was filtered to remove insoluble substance. The ethyl acetate was added to 60 ml and then the liquid was washed with 10% $NaHCO_3$ solution, saturated NaCl solution and dried over $Na_2SO_4$. After the drying agent was removed and part of ethyl acetate was evaporated, the crude product was purified by flash column chromatography (eluent: ethyl acetate:cyclohexane=1:4) to obtain the product as a oil (0.37 g).
$^1$H-NMR (400 MHz, $CDCl_3$): δ 7.64712-7.57181 (m, 2H), 7.31524-7.13747 (m, 8H), 6.99553-6.98669 (m, 2H), 6.03583-6.00112 (m, 1H), 5.04079 (t, 1H, J=3.372 Hz), 4.03332-3.98470 (m, 1H), 3.46631-3.40137 (m, 1H), 3.07737-2.97905 (m, 2H), 2.81385-2.80575 (m, 1H), 2.60288-2.57826 (m, 2H), 2.40946-2.37125 (m, 4H), 2.28307-2.25916 (m, 1H), 2.15384-2.12909 (m, 1H); MS (EI) m/z: 501.0, 392.0, 346.0, 300.0, 256.0, 201.0, 185.0, 154.9, 138.9, 110.0, 91.0, 65.0.

Example 16

Synthesis of (3R)-4-(4-toluenesulfonyl)thiomorpholine-3-carboxylic acid [3-(6-methyl-pyridin-2-yl)]-propyl ester 0.301 g (1 mmol) of (3R)-4-(4-toluenesulfonyl)thiomorpholine-3-carboxylic acid, 0.230 g (1.5 mmol) of 3-(6-methyl-pyridin-2-yl)-propanol, 0.088 g (0.33 mmol) of CAS, 0.227 g (1.2 mmol) of DCC and 0.04 g (0.33 mmol) of DMAP were dissolved in 15 mL of $CH_2Cl_2$. The mixture was stirred for 24 h at room temperature. The solid was filtrated and the solvent was evaporated. The residual was dissolved in a suitable amount of ethyl acetate (20 ml) and then the mixture was filtered to remove insoluble substance. The ethyl acetate was added to 60 ml and then the liquid was washed with 10% $NaHCO_3$ solution, saturated NaCl solution and dried over $Na_2SO_4$. After the drying agent was removed and part of ethyl acetate was evaporated, the crude product was purified by flash column chromatography (eluent: ethyl acetate:cyclohexane=1:1) to obtain the product as a oil (0.23 g).

$^1$H-NMR (400 MHz, $CDCl_3$): δ 7.6656(d, 2H, J=8.30 Hz,), 7.4728 (t, 1H, J=7.64 Hz), 7.2650(d, 2H, J=8.12 Hz), 6.9460 (dd, 2H, J=7.64 Hz), 5.0402 (t, 1H, J=3.36), 4.1435-4.0560 (m, 2H), 4.0394-3.9971 (m, 1H), 3.4897-3.45 25 (m, 1H), 3.0141-3.0037 (m, 1H), 2.9842-2.9402 (m, 1H), 2.8000-2.7272 (m, 3H), 2.5152 (s, 3H), 2.3985-2.3680 (m, 4H), 2.0002-1.9645 (m, 2H); MS (EI) m/z: 435.1, 361.1, 280.1, 256.0, 206.1,155.0, 134.0, 120.0, 107.1, 91.0, 77.0, 65.0.

Example 17

Synthesis of (3R)-4-(4-toluenesulfonyl)thiomorpholine-3-carboxylic acid [N-ethyl-N-3-(3-methyl)phenyl]-ethyl ester 0.301 g (1 mmol) of (3R)-4-(4-toluenesulfonyl)thiomorpholine-3-carboxylic acid, 0.290 g (1.5 mmol) of N-ethyl-N-3-(3-methyl)phenyl-ethanol, 0.088 g (0.33 mmol) of CAS, 0.227 g (1.2 mmol) of DCC and 0.04 g (0.33 mmol) of DMAP were dissolved in 15 mL of $CH_2Cl_2$. The mixture was stirred for 24 h at room temperature. The solid was filtrated and the solvent was evaporated. The residual was dissolved in a suitable amount of ethyl acetate (20 ml) and then the mixture was filtered to remove insoluble substance. The ethyl acetate was added to 60 ml and then the liquid was washed with 10% $NaHCO_3$ solution, saturated NaCl solution and dried over $Na_2SO_4$. After the drying agent was removed and part of ethyl acetate was evaporated, the crude product was purified by flash column chromatography (eluent: ethyl acetate:cyclohexane=1:4) to obtain the product as a oil (0.26 g).

$^1$H-NMR (400 MHz, $CDCl_3$): δ 7.6328(d, 2H, J=8.64 Hz), 7.2266(d, 2H, J=8.68 Hz), 7.1124-7.0718 (m, 1H), 6.5235-6.4769 (m, 3H), 5.0218 (t, 1H,J=3.36 Hz), 4.2291-4.1853 (m, 1H), 4.1530-4.1093 (m, 1H), 4.0146-3.9662 (m, 1H), 3.4556-3.4073 (m, 3H), 3.3813-3.3020 (m, 2H), 2.9381 (d, 2H J=3.68 Hz), 2.7606-2.7020 (m, 1H), 2.6938 (s, 3H), 2.3649-2.3449 (m, 1H), 2.0165 (s, 3H), 1.1171 (t, 3H, J=6.98 Hz); MS (EI) m/z: 462.1, 447.0, 255.9, 162.1,148.0, 134.0, 120.0, 101.0, 83.9, 65.0.

Example 18

Synthesis of (3R)-4-(4-toluenesulfonyl)thiomorpholine-3-carboxylic acid (1,3-diphenylmethyloxy)-isopropyl ester 0.301 g (1 mmol) of (3R)-4-(4-toluenesulfonyl)thiomorpholine-3-carboxylic acid, 0.420 g (1.5 mmol) of (1,3-diphenylmethyloxy)-isopropanol, 0.088 g (0.33 mmol) of CAS, 0.227 g (1.2 mmol) of DCC and 0.04 g (0.33 mmol) of DMAP were dissolved in 15 mL of $CH_2Cl_2$. The mixture was stirred for 24 h at room temperature. The solid was filtrated and the solvent was evaporated. The residual was dissolved in a suitable amount of ethyl acetate (20 ml) and then the mixture was filtered to remove insoluble substance. The ethyl acetate was added to 60 ml and then the liquid was washed with 10% $NaHCO_3$ solution, saturated NaCl solution and dried over $Na_2SO_4$. After the drying agent was removed and part of ethyl acetate was evaporated, the crude product was purified by flash column chromatography (eluent: ethyl acetate:cyclohexane=1:6) to obtain the product as a oil (0.50 g).

$^1$H-NMR (400 MHz, $CDCl_3$): δ 7.6356(d, 2H, J=8.36 Hz), 7.3432-7.2666 (brs, 10H), 7.1849(d, 2H, J=8.40 Hz), 5.1879-5.1623 (m, 1H), 5.0965 (t, 1H, J=3.20 Hz), 4.5299-4.4579 (m, 4H), 3.9542-3.9127 (m, 1H) 3.6547-3.6179 (m, 1H) 3.5932-3.5497 (m, 3H), 3.5014-3.4300 (m, 1H), 3.0354-3.0247 (m, 1H), 2.9998-2.9558 (m, 1H), 2.8109-2.7379 (m, 1H), 2.3696 (s, 3H), 2.3139-2.2757 (m, 1H).

Example 19

Synthesis of (3R)-4-(4-toluenesulfonyl)thiomorpholine-3-carboxylic acid (thiophen-2-yl)-ethyl ester 0.301 g (1 mmol) of (3R)-4-(4-toluenesulfonyl)thiomorpholine-3-carboxylic acid, 0.190 g (1.5 mmol) of (thiophen-2-yl)-ethanol, 0.088 g (0.33 mmol) of CAS, 0.227 g (1.2 mmol) of DCC and 0.04 g (0.33 mmol) of DMAP were dissolved in 15 mL of $CH_2Cl_2$. The mixture was stirred for 24 h at room temperature. The solid was filtrated and the solvent was evaporated. The residual was dissolved in a suitable amount of ethyl acetate (20 ml) and then the mixture was filtered to remove insoluble substance. The ethyl acetate was added to 60 ml and then the liquid was washed with 10% $NaHCO_3$ solution, saturated NaCl solution and dried over $Na_2SO_4$. After the drying agent was removed and part of ethyl acetate was evaporated, the crude product was purified by flash column chromatography (eluent: ethyl acetate:cyclohexane=1:6) to obtain the product as a oil (0.28 g).

$^1$H-NMR (400 MHz, $CDCl_3$): δ 7.6518(d, 2H, J=6.60 Hz), 7.6601-7.6392 (m, 2H).7.1611 (dd, 1H, $J_1$=7.28 Hz, $J_2$=0.68 Hz), 6.9325 (dd, 1H, $J$=3.50Hz, $J_2$=5.08 Hz), 6.8210-6.8111 (m, 1H), 5.0563 (t, 1H, J=3.36 Hz), 4.3347-4.2140 (m, 2H), 4.0086-3.9596 (m, 1H), 3.4014-3.3301 (m, 1H), 3.0775-2.9831 (m, 4H), 2.7804-2.7479 (m, 1H), 2.4220 (s, 3H), 2.3687-2.3300 (m, 1H); MS (EI) m/z: 411.1, 256.1, 155.1, 139.1, 110.1, 91.1, 77.1, 65.1.

Example 20

Synthesis of (3R)-4-(4-toluenesulfonyl)thiomorpholine-3-carboxylic acid (3-phenoxy)-propyl ester 0.301 g (1 mmol) of (3R)-4-(4-toluenesulfonyl)thiomorpholine-3-carboxylic acid, 0.190 g (1.5 mmol) of (3-phenoxy)-propanol, 0.088 g (0.33 mmol) of CAS, 0.227 g (1.2 mmol) of DCC and 0.04 g (0.33 mmol) of DMAP were dissolved in 15 mL of $CH_2Cl_2$. The mixture was stirred for 24 h at room temperature. The solid was filtrated and the solvent was evaporated. The residual was dissolved in a suitable amount of ethyl acetate (20 ml) and then the mixture was filtered to remove insoluble substance. The ethyl acetate was added to 60 ml and then the liquid was washed with 10% $NaHCO_3$ solution, saturated NaCl solution and dried over $Na_2SO_4$. After the drying agent was removed and part of ethyl acetate was evaporated, the crude product was purified by flash column chromatography (eluent: ethyl acetate:cyclohexane=1:4) to obtain the product as a oil (0.39 g).

$^1$H-NMR (400 MHz, $CDCl_3$): δ 7.6586 (d, 2H, J=8.40 Hz), 7.2822-7.2507 (m, 4H) 6.9676-6.9307 (m, 1H). 6.8864-6.8648 (m, 2H).5.0614 (t, 1H, J=3.40 Hz), 4.2890-4.2472 (m, 2H), 4.0024-3.9641 (m, 3H), 3.4320-3.3606 (m, 1H), 3.0216-2.9506 (m, 2H), 2.8043-2.7313 (m, 1H), 2.4034 (s,

3H), 2.3621-2.3239 (m, 1H), 2.0710-2.0223 (m, 2H); MS (EI) m/z: 435.5, 342.4, 280.5, 256.4, 227.5, 186.4, 155.3, 139.3, 101.3, 77.2.

Example 21

Synthesis of (3R)-4-(4-toluenesulfonyl)thiomorpholine-3-carboxylic acid [1-phenyl-1-(3-tolyl)]-methyl ester 0.200 g (0.6 mmol) of (3R)-4-(4-toluenesulfonyl)thiomorpholine-3-carboxylic acid, 0.196 g (1.0 mmol) of 1-phenyl-1-(3-tolyl)-methanol, 0.088 g (0.33 mmol) of CAS, 0.227 g (1.2 mmol) of DCC and 0.04 g (0.33 mmol) of DMAP were dissolved in 15 mL of $CH_2Cl_2$. The mixture was stirred for 24 h at room temperature. The solid was filtrated and the solvent was evaporated. The residual was dissolved in a suitable amount of ethyl acetate (20 ml) and then the mixture was filtered to remove insoluble substance. The ethyl acetate was added to 60 ml and then the liquid was washed with 10% $NaHCO_3$ solution, saturated NaCl solution and dried over $Na_2SO_4$. After the drying agent was removed and part of ethyl acetate was evaporated, the crude product was purified by flash column chromatography (eluent: ethyl acetate:cyclohexane=1:9) to obtain the product as a oil (0.24 g).

$^1$H-NMR (400 MHz, $CDCl_3$): δ 7.5729-7.5521 (m, 2H), 7.3578-7.3008 (m, 5H), 7.2962-7.2405 (m, 4H), 7.1499-7.1005 (m, 2H), 6.7798(d, 1H, J=3.04 Hz), 5.1206 (t, 1H, J=3.40 Hz), 3.9791(d, 1H, J=13.6 Hz), 3.4465-3.4314 (m, 1H) 3.1366-3.0893 (m, 1H), 3.0466-3.0023 (m, 1H), 2.8158-2.7431 (m, 1H), 2.3658-2.3578 (m, 4H), 2.3177-2.3098 (m, 3H); MS (EI) m/z: 481.5, 300.4, 256.4, 181.3, 155.3, 139.3, 115.3, 91.2, 65.2.

Example 22

Synthesis of (3R)-4-(4-toluenesulfonyl)thiomorpholine-3-carboxylic acid [1-methyl-1-(3-trifluoromethylphenyl)]-methyl ester 0.200 g (0.6 mmol) of (3R)-4-(4-toluenesulfonyl)thiomorpholine-3-carboxylic acid, 0.190 g (1.0 mmol) of 1-methyl-1-(3-trifluoromethylphenyl)-methanol, 0.088 g (0.33 mmol) of CAS, 0.227 g (1.2 mmol) of DCC and 0.04 g (0.33 mmol) of DMAP were dissolved in 15 mL of $CH_2Cl_2$. The mixture was stirred for 24 h at room temperature. The solid was filtrated and the solvent was evaporated. The residual was dissolved in a suitable amount of ethyl acetate (20 ml) and then the mixture was filtered to remove insoluble substance. The ethyl acetate was added to 60 ml and then the liquid was washed with 10% $NaHCO_3$ solution, saturated NaCl solution and dried over $Na_2SO_4$. After the drying agent was removed and part of ethyl acetate was evaporated, the crude product was purified by flash column chromatography (eluent: ethyl acetate:cyclohexane=1:9) to obtain the product as a oil (0.13 g).

$^1$H-NMR (400 MHz, $CDCl_3$): δ 7.6060-7.5522 (m, 3H), 7.5157-7.4522 (m, 3H), 7.1652(d, 2H, J=8.00 Hz), 5.8728 (dd, 1H, $J_1$=13.20 Hz, $J_2$=6.64 Hz), 5.0743 (t, 1H, J=3.44 Hz), 4.0359-3.9869 (m, 1H), 3.4477-3.3767 (m, 1H), 3.1175-3.0714 (m, 1H), 3.0514-3.0072 (m, 1H), 2.8418-2.7085 (m, 1H), 2.4092 (s, 1H), 2.3747 (s, 3H), 1.4918 (d, 3H, J=6.64 Hz); MS (EI) m/z: 473.4, 318.4, 300.4, 256.4, 173.4, 155.3, 133.3, 91.3, 65.2.

Example 23

Synthesis of (3R)-4-(4-toluenesulfonyl)thiomorpholine-3-carboxylic acid 4-nitrobenzyl ester 0.200 g (0.6 mmol) of (3R)-4-(4-toluenesulfonyl)thiomorpholine-3-carboxylic acid, 0.190 g (1.0 mmol) of 4-nitrobenzyl alcohol, 0.088 g (0.33 mmol) of CAS, 0.227 g (1.2 mmol) of DCC and 0.04 g (0.33 mmol) of DMAP were dissolved in 15 mL of $CH_2Cl_2$. The mixture was stirred for 24 h at room temperature. The solid was filtrated and the solvent was evaporated. The residual was dissolved in a suitable amount of ethyl acetate (20 ml) and then the mixture was filtered to remove insoluble substance. The ethyl acetate was added to 60 ml and then the liquid was washed with 10% $NaHCO_3$ solution, saturated NaCl solution and dried over $Na_2SO_4$. After the drying agent was removed and part of ethyl acetate was evaporated, the crude product was purified by flash column chromatography (eluent: ethyl acetate:cyclohexane=1:9) to obtain the product as a oil (0.29 g).

$^1$H-NMR (400 MHz, $CDCl_3$): δ 8.1866(d, 2H, J=8.68 Hz), 7.6521(d, 2H, J=8.68 Hz), 7.4561(d, 2H, J=8.44 Hz), 7.2539(d, 2H, J=8.36 Hz), 5.2457-5.2062 (m, 2H), 5.1662 (t, 1H, J=3.6 Hz), 4.0484-3.9997 (m, 1H), 3.4650-3.3935 (m, 1H), 3.1092-3.0637 (m, 1H), 3.0133-2.9689 (m, 1H), 2.7844-2.7113 (m, 1H), 2.4157-2.3775 (m, 4H); MS (EI) m/z: 437.0, 281.0, 256.1,184.0, 154.9, 135.9, 91.0, 65.0.

Example 24

Synthesis of (3R)-4-(4-toluenesulfonyl)thiomorpholine-3-carboxylic acid 2-methoxybenzyl ester 0.200 g (0.6 mmol) of (3R)-4-(4-toluenesulfonyl)thiomorpholine-3-carboxylic acid, 0.138 g (1.0 mmol) of 2-methoxybenzyl alcohol, 0.088 g (0.33 mmol) of CAS, 0.227 g (1.2 mmol) of DCC and 0.04 g (0.33 mmol) of DMAP were dissolved in 15 mL of $CH_2Cl_2$. The mixture was stirred for 24 h at room temperature. The solid was filtrated and the solvent was evaporated. The residual was dissolved in a suitable amount of ethyl acetate (20 ml) and then the mixture was filtered to remove insoluble substance. The ethyl acetate was added to 60 ml and then the liquid was washed with 10% $NaHCO_3$ solution, saturated NaCl solution and dried over $Na_2SO_4$. After the drying agent was removed and part of ethyl acetate was evaporated, the crude product was purified by flash column chromatography (eluent: ethyl acetate:cyclohexane=1:6) to obtain the product as a oil (0.19 g).

$^1$H-NMR (400 MHz, $CDCl_3$): δ 7.6450-7.6152 (m, 2H), 7.3286-7.2851 (m, 1H), 7.2068-7.1789 (m, 3H), 6.9372-6.9166 (m, 1H), 6.8642(d, 1H, J=8.16 Hz), 5.1842(d, 1H, J=24.1 Hz), 5.1054-5.0535 (m, 2H), 4.0126-3.9637 (m, 1H), 3.7975 (s, 3H), 3.5146-3.4432 (m, 1H), 3.0867-3.0412 (m, 1H), 3.0026-2.9585 (m, 1H), 2.8240-2.7513 (m, 1H), 2.3782-2.3414 (m, 4H); MS (EI) m/z: 421.0, 300.0, 255.8, 241.0, 211.0, 154.9, 138.9, 121.0, 91.0, 65.0.

Example 25

Synthesis of (3R)-4-(4-toluenesulfonyl)thiomorpholine-3-carboxylic acid (3-ethoxy-2-methoxy)-benzyl ester 0.200 g (0.6 mmol) of (3R)-4-(4-toluenesulfonyl)thiomorpholine-3-carboxylic acid, 0.190 g (1.0 mmol) of (3-ethoxy-2-methoxy)-benzyl alcohol, 0.088 g (0.33 mmol) of CAS, 0.227 g (1.2 mmol) of DCC and 0.04 g (0.33 mmol) of DMAP were dissolved in 15 mL of $CH_2Cl_2$. The mixture was stirred for 24 h at room temperature. The solid was filtrated and the solvent was evaporated. The residual was dissolved in a suitable amount of ethyl acetate (20 ml) and then the mixture was filtered to remove insoluble substance. The ethyl acetate was added to 60 ml and then the liquid was washed with 10% $NaHCO_3$ solution, saturated NaCl solution and dried over $Na_2SO_4$. After the drying agent was removed and part of ethyl acetate was evaporated, the crude product was purified by flash column chromatography (eluent: ethyl acetate:cyclohexane=1:9) to obtain the product as a oil (0.19 g).

$^1$H-NMR (400 MHz, $CDCl_3$): δ 7.6325(d, 2H, J=8.28 Hz), 7.2212(d, 2H, J=8.24 Hz), 6.8342-6.7827 (m, 3H), 5.6953-5.0652 (m, 2H), 4.9789(d, 1H, J=24.00 Hz), 4.0876 (dd, 2H), $J_1$=6.99 Hz, $J_2$=13.99 Hz), 4.0048-3.9569 (m, 1H), 3.8465 (s, 3H), 3.4636-3.3924 (m, 1H), 3.0680-3.0339 (m, 1H), 2.9730-2.9289 (m, 1H), 2.7775-2.7047 (m, 1H), 2.3920-2.3320 (m, 4H), 1.4517 (t, 3H, J=11.00 Hz); MS (EI) m/z: 465.0, 256.0, 165.0, 137.0, 101.0, 91.0, 65.0.

Example 26

Synthesis of (3R)-4-(4-toluenesulfonyl)thiomorpholine-3-carboxylic acid 4-phenylbenzyl ester 0.200 g (0.6 mmol) of (3R)-4-(4-toluenesulfonyl)thiomorpholine-3-carboxylic acid, 0.184 g (1.0 mmol) of 4-phenylbenzyl alcohol, 0.088 g (0.33 mmol) of CAS, 0.227 g (1.2 mmol) of DCC and 0.04 g (0.33 mmol) of DMAP were dissolved in 15 mL of $CH_2Cl_2$. The mixture was stirred for 24 h at room temperature. The solid was filtrated and the solvent was evaporated. The residual was dissolved in a suitable amount of ethyl acetate (20 ml) and then the mixture was filtered to remove insoluble substance. The ethyl acetate was added to 60 ml and then the liquid was washed with 10% $NaHCO_3$ solution, saturated NaCl solution and dried over $Na_2SO_4$. After the drying agent was removed and part of ethyl acetate was evaporated, the crude product was purified by flash column chromatography (eluent: ethyl acetate:cyclohexane=1:9) to obtain the product as a oil (0.29 g).

$^1$H-NMR (400 MHz, $CDCl_3$): δ 7.6067(d, 2H, J=8.30 Hz), 7.4254-7.3367 (m, 6H), 7.3041-7.2364 (m, 3H), 7.1667 (d, 2H, J=8.00 Hz), 5.0923-4.9933 (m, 3H), 3.9882-3.9393 (m, 1H), 3.4185-3.3471 (m, 1H), 2.9487(d, 2H, J=3.40 Hz), 2.7940-2.7210 (m, 1H), 2.3549-2.3195 (m, 4H); MS (EI) m/z: 467.0, 422.0, 312.0, 255.9, 167.0, 115.0, 91.0, 65.0.

Example 27

Synthesis of 2-{[(3R)-1,1-dioxo-4-(4-toluenesulfonyl)thiomorpholine-3-carbonyl]amino}-4-methyl-pentanoic acid ethyl ester 1.0 mmol of 2-{[(3R)-4-(4-toluenesulfonyl)thiomorpholine-3-carbonyl]amino}-4-methyl-pentanoic acid ethyl ester was dissolved in 20 ml of $CH_2Cl_2$, and a solution (10 ml) of MCPBA (2 mmol) in $CH_2Cl_2$. The mixture was stirred room temperature for 12 h and then was washed with saturated $NaHCO_3$ solution (15, 15, 10 ml), and dried over $Na_2SO_4$. After the drying agent was removed and part of $CH_2Cl_2$ was evaporated, the crude product was purified by flash column chromatography (eluent: ethyl acetate:cyclohexane=1:2) to obtain the product as a white solid (0.40 g).

$^1$H-NMR (400 MHz, $CDCl_3$): δ 7.80407 (dd, 2H, $J_1$=8.308 Hz, 8.320 Hz, $J_2$=12.386 Hz), 7.40339 (dd, 2H, $J_1$=2.648 Hz, 2.588 Hz, $J_2$=8.266 Hz), 6.68488(d, 0.5H, J=8.208 Hz), 6.57464(d, 0.5H, J=8.872 Hz), 5.06677-5.02375 (m, 1H), 4.65100-4.58180 (m, 1H), 4.50723-4.38399 (m, 1H), 4.22503-4.15725 (m, 2H), 4.05936-3.97473 (m, 1.5H), 3.79537-3.73058 (m, 0.5H), 3.01496-2.85539 (m, 3H), 2.47240 (s, 3H), 1.63840-1.40100 (m, 3H), 1.30660-1.25900 (m, 3H), 0.94960-0.88250 (m, 6H); MS (EI) m/z: 473.3, 381.2, 302.2, 254.2, 238.0, 192.1,180.2, 169.9, 155.2, 90.5.

Example 28

The neurotrophic activity of compounds of the present invention can be determined through several biological models in vitro, e.g. the model of chick embryos dorsal root ganglion cultures free of serum in vitro.

In a sterile environment, dorsal root ganglia were dissected from chick embryos of 8 days gestation and inoculated in rat rail collagen coated culture bottles (5 to 6 dorsal root ganglia per bottle, and two bottles per dosage). After 1 hour of attachment in a 37° C., 5% $CO_2$ incubator, NGF (0.30 ng/ml) containing culture medium free of serum (DMEM) and the compound of example 4 of the present invention were added. The control groups were treated only with the same amount of NGF and culture medium. After further incubated in a incubator as described above for 48 h, the ganglia were observed for growth of the processes around dorsal root ganglia under phase contrast with an inverted microscope, and were scored based on the neurite processes (ganglion with free processes: 0; ganglion with rare processes: 1; ganglion with long or dense processes: 2; ganglion with very long or dense processes: 3). The results of the experiments showed that the illustrative compound of example 4 of the present invention at a concentration of from 0.1 to 1.0 pmol/L promote the growth of chick embryos dorsal root ganglia processes. The representative micrographic pictures showing that compound of example 4 promotes the growth of chick embryos dorsal root ganglia processes were give in FIG. 1. The results of illustrative compound of example 4 at different concentrations promoting the growth of chick embryos dorsal root ganglia processes were outlined in table 1, wherein the scoring is the average scoring of 20 ganglia.

TABLE 1

| Groups | Average scoring |
|---|---|
| culture medium + NGF (0.3 ng/mL) | 1.0 |
| compound of example 4 (0.1 pM) + NGF (0.3 ng/mL) | 2.15 |
| compound of example 4 (1.0 pM) + NGF (0.3 ng/mL) | 2.16 |
| compound of example 4 (10 pM) + NGF (0.30 ng/mL) | 1.50 |

Figure 1:
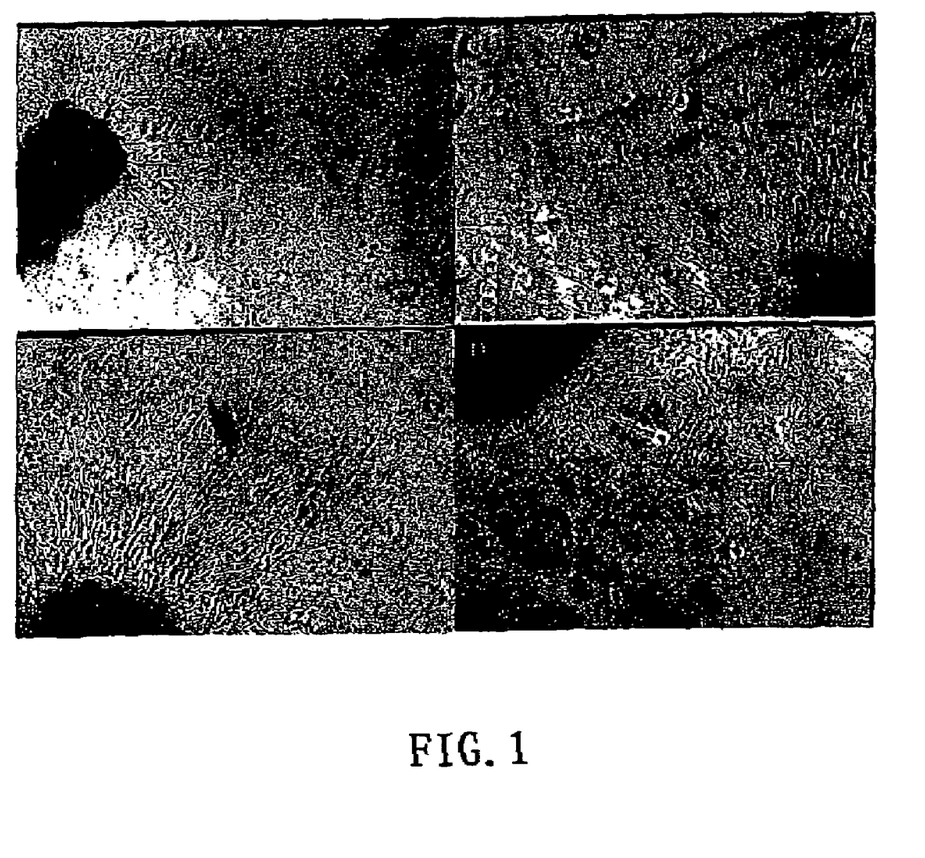
FIG. 1 shows photomicrographs of chick embryo dorsal root ganglion cultures after incubation with the illustrative compound of Example 4.

FIG. 1 show the results of illustrative compound of example 4 at different concentrations promoting the growth of chick embryos dorsal root ganglia processes.

Example 29

Figure 2:
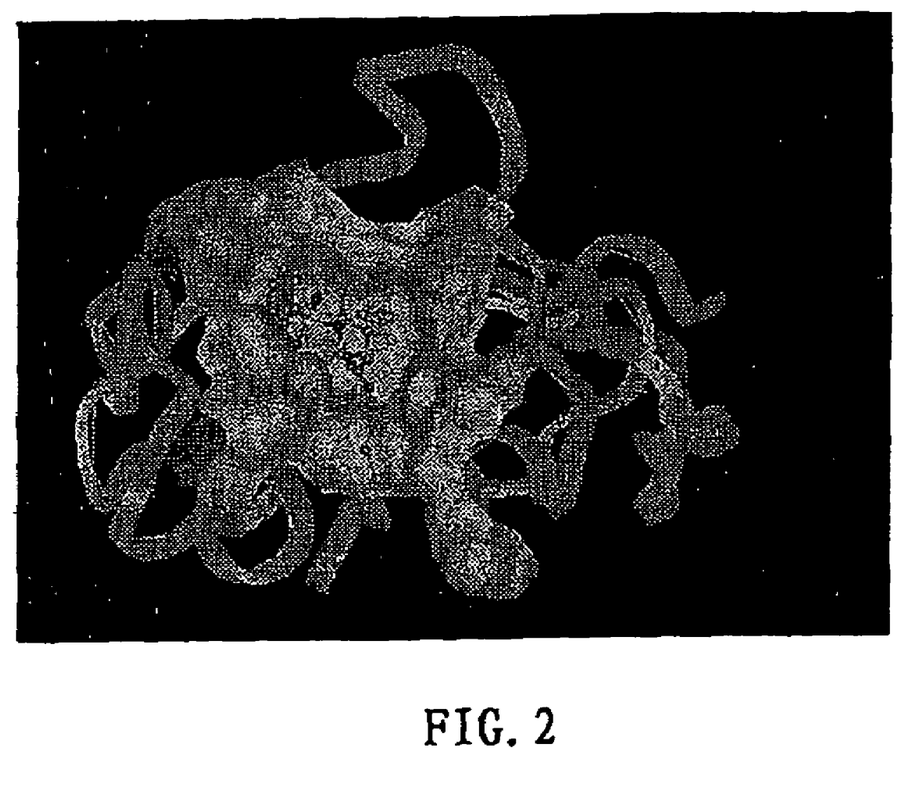
FIG. 2 shows an X-ray diffraction structure diagram of the composite 000308-FKBP12.

The combination situations of the compounds of the present invention can be estimated according to the structures obtained by the X-ray diffraction of the monocrystalline of the composite formed between said compounds and FKBP12 protein, and the results are depicted in FIG. 2. FIG. 2 is the X-ray diffraction structure diagram of the composite 000308-FKBP12.

Example 30

The neurotrophic activity of the compounds of the present invention can also be determined in several animal pharmacological models in vivo, such as the model of adult mice sympathetic nerve endings damaged by 6-hydroxy-dopamine (6-OHDA).

Kunming species female mice (♀) having a body weight of 18-22 g are randomly divided into the following groups: normal control group, model control group, FK506 (2 mg/kg) group, and the group of compound of the present invention (5 mg/kg) (10 mice per group). The mice are administrated with 6-OHDA (8 mg/kg) by intraperitoneal injection (ip) before 4 hours and after 4 continuous days of subcutaneous injection (sc) of the compound, while the control groups are administrated with the equivalent quantity of carrier by subcutaneous injection. After two weeks of the last administration, the mice are killed by luxation, and the two submaxillary glands of each of the mice are rapidly excised and weighed, placed in a glass grinder, then is homogenated with a homogenating liquid containing internal-standard, and centrifuged at 2000 g for 30 minutes. 20 μL of the obtained supernatant is directly injected in an HPLC-electrochemical detector to measure the content of noradrenaline (NE) in the submaxillary glands of the mice. The results are shown in FIG. 3.

Figure 3:
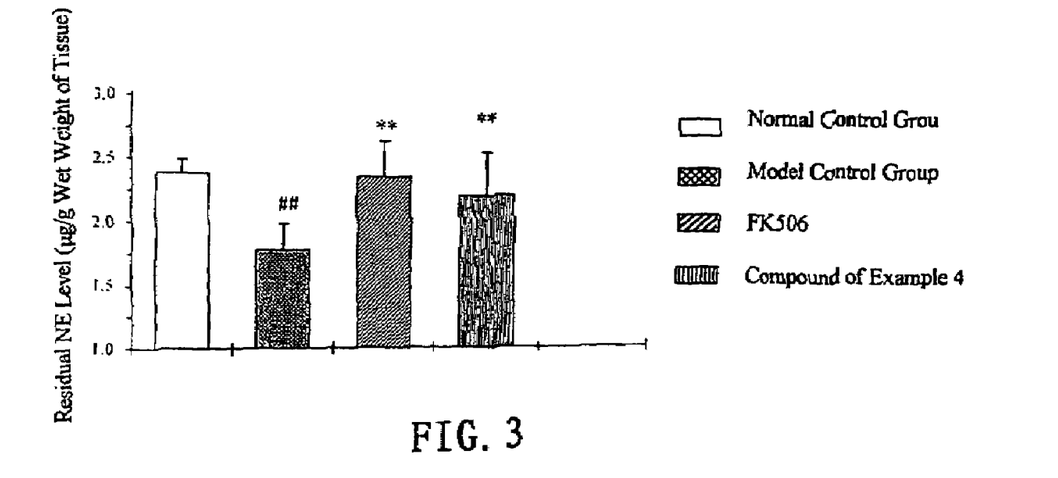
FIG. 3 shows a graph indicating the effect of the representative compound of Example 4 on the amount of residual noradrenaline (NE) in the submaxillary glands of mice whose sympathetic nerve terminals are damaged with 6-OHDA.

FIG. 3 indicates the effect of the representative compound of the Example 4 on the level of residual NE in the submaxillary glands of the mice whose sympathetic nerve terminals are damaged with 6-OHDA. It can be seen that after the administration of 6-OHDA (8 mg/kg) by injection intraperitoneal injection, the content of the residual NE in the submaxillary glands of the mice decreases significantly, and the P<0.01 in comparison with the normal group. The compound of the Example 4 (5 mg/kg) raise the residual NE level in the submaxillary glands of the mice, and alleviate the damage of 6-OHDA to the sympathetic nerve terminal endings. (##P<0.01 vs normal control group, **P<0.01 vs model control group).

REFERENCES

1. Starzl T E, Makowka L, Todo S. FK-506: A potential breakthrough in immunosuppression. Transplant Proc, 1987, 19: S3-S104.
2. Maki N, Sekiguchi F, Nishimaki J, et al. Complementary DNA encoding the human T-cell FK506-binding protein, a peptidylprolyl cis-trans isomerase distinct from cyclophilin. Proc Natl Acad Sci USA, 1990, 87: 5440-5443.
3. Steiner J P, Dawson T M, Fotuhi M, et al. High brain densities of the immunophilin FKBP colocalized with calcineurin. Nature, 1992, 358: 584-587.
4. Sharkey J, Butcher S P. Immunophilins mediate the neuroprotective effects of FK506 in focal celebral ischaemia. Nature, 1994, 371: 336-339.
5. Lyons, W E, George E B, Dawson T M, et al. Immunosuppresant FK506 promotes neurite outgrowth in cultures of PC-12 cells and sensory ganglia. Proc Natl Acad Sci USA, 1994, 91: 3191-3195.
6. Gold B G, Storm-Dickerson T, Austin D R. The immunosuppressant FK506 increases functional recovery and nerve regeneration following peripheral nerve injury. Restor Neurol Neurosci, 1994, 6: 287.
7. Gold B G, Katoh K, Storm-Dickerson T. The immunosuppressant FK506 increases the rate of axonal regeneration in rat sciatic nerve. J Neurosci, 1995, 15: 7509-7516.
8. Kopp J B, Klotman P E. Cellular and molecular mechanisms of cyclosporin nephrotoxicity. J Am Soc Nephrol, 1991,1:162-179.
9. De Groen D G, Aksamit A J, Rakela J, et al. Central nervous system toxicity after liver transplantation. N Engl J Med, 1987, 317: 861-866.
10. Kahan B D. Drug therapy: cyclosporine. N Engl J Med, 1989, 321: 1725-1738.

What is claimed is:

1. A compound of formula (I):

$$\text{(I)}$$

or a pharmaceutically acceptable salt or a hydrate thereof, wherein

X is S, SO or $SO_2$;

Y is O or S;

Z is $CR_2$, O or $NR_4$, wherein $R_4$ is hydrogen or $C_1$-$C_6$ alkyl;

$R_1$ is straight or branched chain $C_1$-$C_8$ alkyl, straight or branched chain $C_2$-$C_8$ alkenyl, $C_3$-$C_8$ cycloalkyl, $C_5$-$C_7$ cycloalkenyl, or $Ar_1$, wherein alkyl or alkenyl chain may be unsubstituted or substituted with one or more of the following groups: $C_3$-$C_8$ cycloalkyl, $C_5$-$C_7$ cycloalkenyl, or $Ar_2$;

$R_2$ is straight or branched chain $C_1$-$C_{10}$ alkyl, straight or branched chain $C_2$-$C_{10}$ alkenyl, $C_3$-$C_8$ cycloalkyl, $C_5$-$C_7$ cycloalkenyl, and $Ar_1$, wherein alkyl or alkenyl chain may be unsubstituted or substituted with one or more of the following groups: $C_3$-$C_8$ cycloalkyl, $C_5$-$C_7$ cycloalkenyl, or $Ar_2$, in addition, wherein a part of carbon atoms of alkyl or alkenyl can be replaced by nitrogen or oxygen atoms;

$Ar_1$ and $Ar_2$ are independently selected from mono-, di-, or tricyclic aromatic carbocyclic ring and heterocyclic ring containing 1 to 6 heteroatoms selected from the group consisting of O, S and N, wherein each single ring is 5-membered or 6-membered, and said ring may be unsubstituted or substituted in one to five position(s) with 1 to 3 following groups: halogens, nitro, hydroxy, hydroxymethyl, trifluoromethyl, trifluoromethoxyl, straight or branched chain $C_1$-$C_6$ alkyl, straight or branched chain $C_2$-$C_6$ alkenyl, $C_1$-$C_4$ alkoxy, $C_2$-$C_4$ alkenoxy, phenoxy, benzyloxy, carboxyl or amino;

wherein the relative configuration of group —$SO_2R_1$ to group —$CYZR_2$ is a trans-configuration; and wherein said compound is selected from the group consisting of:

2-{[(3R)-4-(4-toluenesulfonyl)thiomorpholine-3-carbonyl]amino}-3-phenyl-propionic acid benzyl ester, 2-{[(3R)-4-(4-toluenesulfonyl)thiomorpholine-3-carbonyl]amino}-3-methyl-butyric acid benzyl ester, 2-{[(3R)-4-(4-toluenesulfonyl)thiomorpholine-3-carbonyl]amino}-4-methyl-pentanoic acid benzyl ester, 2-{[(3R)-4-(4-toluenesulfonyl)thiomorpholine-3-carbonyl]amino}-4-methyl-pentanoic acid ethyl ester, (3R)-4-(4-toluenesulfonyl)thiomorpholine-3-carboxylic acid [3-(pyridin-3-yl)]-propyl ester, (3R)-4-(4-toluenesulfonyl)thiomorpholine-3-carboxylic acid [N-methyl-N-(pyridin-2-yl)]-ethyl ester,
(3R)-4-(4-toluenesulfonyl)thiomorpholine-3-carboxylic acid phenyipropyl ester,
(3R)-4-(4-toluenesulfonyl)thiomorpholine-3-carboxylic acid (2-trifluoromethyl)-phenylethyl ester,
(3R)-4-(4-toluenesulfonyl)thiomorpholine-3-carboxylic acid (N-methyl-N-benzyl)-ethyl ester,
(3R)-4-(4-toluenesulfonyl)thiomorpholine-3-carboxylic acid (3-phenyl)-allyl ester,
(3R)-4-(4-toluenesulfonyl)thiomorpholine-3-carboxylic acid (3-cyclohexyl)-propyl ester,
(3R)-4-(4-toluenesulfonyl)thiomorpholine-3-carboxylic acid (1,3-diphenyl)-propyl ester,
(3R)-4-(4-toluenesulfonyl)thiomorpholine-3-carboxylic acid (1-p-methoxyphenyl-3-phenyl)-propyl ester,
(3R)-4-(4-toluenesulfonyl)thiomorpholine-3-carboxylic acid (1-p-fluorophenyl-3-phenyl)-propyl ester,
(3R)-4-(4-toluenesulfonyl)thiomorpholine-3-carboxylic acid [3-phenyl-1-(thiophen-2-yl)]-propyl ester,
(3R)-4-(4-toluenesulfonyl)thiomorpholine-3-carboxylic acid [3-(6-methyl-pyridin-2-yl)]-propyl ester,
(3R)-4-(4-toluenesulfonyl)thiomorpholine-3-carboxylic acid [N-ethyl-N-3-(3-methyl)phenyl]-ethyl ester,
(3R)-4-(4-toluenesulfonyl)thiomorpholine-3-carboxylic acid (1,3-diphenylmethyloxy)-isopropyl ester,
(3R)-4-(4-toluenesulfonyl)thiomorpholine-3-carboxylic acid (thiophen-2-yl)-ethyl ester,
(3R)-4-(4-toluenesulfonyl)thiomorpholine-3-carboxylic acid (3-phenoxy)-propyl ester,
(3R)-4-(4-toluenesulfonyl)thiomorpholine-3-carboxylic acid [1-phenyl-1-(3-tolyl)]-methyl ester,
(3R)-4-(4-toluenesulfonyl)thiomorpholine-3-carboxylic acid [1-methyl-1-(3-trifluoromethylphenyl)]-methyl ester,
(3R)-4-(4-toluenesulfonyl)thiomorpholine-3-carboxylic acid 4-nitrobenzyl ester,
(3R)-4-(4-toluenesulfonyl)thiomorpholine-3-carboxylic acid 2-methoxybenzyl ester,
(3R)-4-(4-toluenesulfonyl)thiomorpholine-3-carboxylic acid (3-ethoxy-2-methoxy)-benzyl ester,
(3R)-4-(4-toluenesulfonyl)thiomorpholine-3-carboxylic acid 4-phenylbenzyl ester, and
2-{[(3R)-1,1-dioxo-4-(4-toluenesulfonyl)thiomorpholine-3-carbonyl]amino}-4-methyl-pentanoic acid ethyl ester.

2. A pharmaceutical composition comprising an effective amount of a compound or a pharmaceutically acceptable salt or a hydrate thereof according to claim 1 and a pharmaceutically acceptable carrier or excipient.

3. A method of treating Parkinson's disease and amyotrophic lateral sclerosis comprising the step of administering a therapeutically effective amount of a compound according to claim 1 or a pharmaceutically acceptable salt or a hydrate thereof to patients in need.

* * * * *